(12) United States Patent
Osafune et al.

(10) Patent No.: US 10,472,610 B2
(45) Date of Patent: Nov. 12, 2019

(54) METHOD FOR GENERATING PANCREATIC BUD CELLS AND THERAPEUTIC AGENT FOR PANCREATIC DISEASE CONTAINING PANCREATIC BUD CELLS

(71) Applicant: Kyoto University, Kyoto (JP)

(72) Inventors: Kenji Osafune, Kyoto (JP); Taro Toyoda, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 19 days.

(21) Appl. No.: 15/311,759

(22) PCT Filed: May 20, 2015

(86) PCT No.: PCT/JP2015/064529
§ 371 (c)(1),
(2) Date: Feb. 14, 2017

(87) PCT Pub. No.: WO2015/178431
PCT Pub. Date: Nov. 26, 2015

(65) Prior Publication Data
US 2017/0175082 A1 Jun. 22, 2017

(30) Foreign Application Priority Data
May 21, 2014 (JP) .................................. 2014-105049

(51) Int. Cl.
C12N 5/071 (2010.01)
A61K 35/39 (2015.01)

(52) U.S. Cl.
CPC ............ *C12N 5/0676* (2013.01); *A61K 35/39* (2013.01); *C12N 2501/11* (2013.01); *C12N 2501/117* (2013.01); *C12N 2501/155* (2013.01); *C12N 2501/16* (2013.01); *C12N 2501/41* (2013.01); *C12N 2501/727* (2013.01); *C12N 2501/999* (2013.01); *C12N 2506/02* (2013.01); *Y02A 20/402* (2018.01)

(58) Field of Classification Search
CPC ........... C12N 5/0676; C12N 2501/155; C12N 2501/11; C12N 2501/117; C12N 2501/16; C12N 2501/41; C12N 2501/727; C12N 2501/999; C12N 2506/02; A61K 35/39; Y02A 20/402
See application file for complete search history.

(56) References Cited

U.S. PATENT DOCUMENTS

| | | | |
|---|---|---|---|
| 7,534,608 B2 | 5/2009 | Martinson et al. | |
| 8,048,999 B2 | 11/2011 | Yamanaka et al. | |
| 8,932,853 B2 | 1/2015 | Hosoya et al. | |
| 9,388,386 B2* | 7/2016 | Rezania | C12N 5/0676 |
| 2003/0087919 A1 | 5/2003 | Nagarathnam et al. | |
| 2003/0125344 A1 | 7/2003 | Nagarathnam et al. | |
| 2004/0002507 A1 | 1/2004 | Nagarathnam et al. | |
| 2004/0002508 A1 | 1/2004 | Nagarathnam et al. | |
| 2004/0014755 A1 | 1/2004 | Nagarathnam et al. | |
| 2005/0192304 A1 | 9/2005 | Nagarathnam et al. | |
| 2005/0209261 A1 | 9/2005 | Nagarathnam et al. | |
| 2010/0112691 A1* | 5/2010 | Green | C12N 5/0606 435/377 |
| 2011/0070647 A1 | 3/2011 | Dezawa et al. | |
| 2014/0242693 A1* | 8/2014 | Fryer | C12N 5/0677 435/366 |
| 2016/0289642 A1 | 10/2016 | Osafune et al. | |

FOREIGN PATENT DOCUMENTS

| | | | |
|---|---|---|---|
| JP | 2006-075022 A | 3/2006 | |
| JP | 2009-225661 A | 10/2009 | |
| JP | 2012-507281 A | 3/2012 | |
| JP | 2012-508584 A | 4/2012 | |
| WO | 2002/076976 A2 | 10/2002 | |
| WO | 2003/059913 A1 | 7/2003 | |
| WO | 2003/062225 A1 | 7/2003 | |
| WO | 2003/062227 A1 | 7/2003 | |
| WO | 2004/039796 A1 | 5/2004 | |
| WO | 2005/037197 A2 | 4/2005 | |
| WO | 2007/069666 A1 | 6/2007 | |
| WO | 2009/146408 A1 | 12/2009 | |
| WO | 2010/053472 A1 | 5/2010 | |
| WO | 2010/057039 A2 | 5/2010 | |
| WO | 2011/007900 A1 | 1/2011 | |
| WO | 2011/081222 A1 | 7/2011 | |
| WO | 2013/163739 A1 | 11/2013 | |
| WO | 2013/184888 A1 | 12/2013 | |
| WO | 2014/160413 A1 | 10/2014 | |
| WO | 2015/020113 A1 | 2/2015 | |

(Continued)

OTHER PUBLICATIONS

Zhou et al. A multipotent progenitor domain guides pancreatic organogenesis. Dev Cell. Jul. 2007;13(1):103-14. (Year: 2007).*
Schulz et al. A Scalable System for Production of Functional Pancreatic Progenitors from Human Embryonic Stem Cells. PLoS ONE 7(5): e37004. p. 1-17 (Year: 2012).*
Kunisada et al. Small molecules induce efficient differentiation into insulin-producing cells from human induced pluripotent stem cells. Stem Cell Research. 8, 274-284 (Year: 2012).*
Chmielowiec et al. In Vitro Differentiation and Expansion of Human Pluripotent Stem Cell-Derived Pancreatic Progenitors. Rev Diabet Stud. 2014 Spring; 11(1): 19-34. (Year: 2014).*
Kunisada et al. Small molecules induce efficient differentiation into insulin-producing cells from human induced pluripotent stem cells. Stem Cell Research (2012) 8, 274-284 (Year: 2012).*

(Continued)

*Primary Examiner* — Taeyoon Kim
(74) *Attorney, Agent, or Firm* — Lathrop Gage LLP; James H. Velema, Esq.

(57) ABSTRACT

Provided is a method for generating pancreatic bud cells, having the step of culturing PDX1$^+$/NKX6.1$^-$ cells in a medium containing KGF, EGF and a BMP inhibitor. The culturing step may be performed in suspension cultures or in adherent cultures. When the cells are cultured in adherent cultures, the cells may be cultured in a medium further containing a ROCK inhibitor or a nonmuscle myosin II inhibitor.

13 Claims, 19 Drawing Sheets

(56) References Cited

FOREIGN PATENT DOCUMENTS

| WO | 2015/099134 A1 | 7/2015 |
| WO | 2015/178431 A1 | 11/2015 |
| WO | 2016/010148 A1 | 1/2016 |
| WO | 2016/010153 A1 | 1/2016 |
| WO | 2016/010154 A1 | 1/2016 |
| WO | 2016/010155 A1 | 1/2016 |

OTHER PUBLICATIONS

Abe et al. (1981) "Differentiation of mouse myeloid leukemia cells induced by 1 alpha,25-dihydroxyvitamin D3," Proc. Natl. Acad. Sci. USA. 78(8):4990-4994.

Byrne et al. (2007) "Producing primate embryonic stem cells by somatic cell nuclear transfer," Nature. 450:497-502.

D'Amour et al. (2006) "Production of pancreatic hormone-expressing endocrine cells from human embryonic stem cells," Nature Biotechnology. 24(11):1392-1401.

Dufrane et al. (2010) "Alginate macroencapsulation of pig islets allows correction of streptozotocin-induced diabetes in primates up to 6 months without immunosuppression," Transplantation. 90:1054-1062.

Feng et al. (2008) "Discovery of Substituted 4-(Pyrazol-4-yl)-phenylbenzodioxane-2-carboxamides as Potent and Highly Selective Rho Kinase (Rock-II) Inhibitors," J. Med. Chem. 51:6642-6645.

Genbank Database [online] (Sep. 11, 2016) "Mus musculus left right determination factor 1 (Lefty1), mRNAm," Accession No. NM_010094. National Center for Biotechnology Information. Accessible on the Internet at URL: http://www.ncbi.nlm.nih.gov/nuccore/NM_010094. [Last Accessed Sep. 16, 2016].

Genbank Database [online] (Oct. 9, 2016) "Homo sapiens left-right determination factor 1 (Leftyi), mRNA," Accession No. NM_020997. National Center for Biotechnology Information. Accessible on the Internet at URL: https://www.ncbi.nlm.nih.gov/nuccore/NM_020997. [Last Accessed Mar. 13, 2017].

Hao et al. (2008) "Dorsomorphin, a Selective Small Molecule Inhibitor of BMP Signaling, Promotes Cardiomyogenesis in Embryonic Stem Cells," PLoS ONE. 3(8):e2904. pp. 1-8.

Ishizaki et al. (2000) "Pharmacological properties of Y-27632, a specific inhibitor of rho-associated kinases," Mol. Pharmacol. 57:976-983.

Jiang (2007) "In vitro derivation of functional insulin-producing cells from human embryonic stem cells," Cell Research. 17:333-344.

Kanatsu-Shinohara et al. (2003) "Long-term proliferation in culture and germline transmission of mouse male germline stem cells," Biol. Reprod. 69:612-616.

Kanatsu-Shinohara et al. (2004) "Generation of pluripotent stem cells from neonatal mouse testis," Cell. 119:1001-1012.

Kroon et al. (2008) "Pancreatic endoderm derived from human embryonic stem cells generates glucose-responsive insulin-secreting cells in vivo," Nature Biotechnology. 26(4):443-452.

Kunisada et al. (2012) "Small molecules induce efficient differentiation into insulin-producing cells from human induced pluripotent stem cells," Stem Cell Res. 8(2):274-284.

Maehr et al. (2009) "Generation of pluripotent stem cells from patients with type 1 diabetes," Proc. Natl. Acad. Sci. USA. 106(37):15768-15773.

Matsui et al. (1992) "Derivation of pluripotential embryonic stem cells from murine primordial germ cells in culture," Cell. 70:841-847.

Nakagawa et al. (2008) "Generation of induced pluripotent stem cells without Myc from mouse and human fibroblasts," Nat. Biotechnol. 26:101-106.

Nakajima et al. (2003) "Effect of Wf-536, a novel ROCK inhibitor, against metastasis of B16 melanoma," Cancer Chemother. Pharmacol. 52(4):319-324.

Narumiya et al. (2000) "Use and properties of ROCK-specific inhibitor Y-27632," Methods Enzymol. 32:273-284.

Okita (2011) "A more efficient method to generate integration-free human iPS cells," Nat. Methods. 8:409-412.

Okita et al. (Mar. 2013) "An efficient nonviral method to generate integration-free human-induced pluripotent stem cells from cord blood and peripheral blood cells," Stem Cells. 31(3):458-466.

Qi et al. (2012) "Immunoisolation effect of polyvinyl alcohol (PVA) macroencapsulated islets in type 1 diabetes therapy," Cell Transplant 21:525-534.

Resnik et al. (1992) "Long-term proliferation of mouse primordial germ cells in culture," Nature. 359:550-551.

Rezania et al. (Jun. 27, 2012) "Maturation of human embryonic stem cell-derived pancreatic progenitors into functional islets capable of treating pre-existing diabetes in mice," Diabetes. 61(8):2016-2029.

Sasaki et al. (2002) "The novel and specific Rho-kinase inhibitor (S)-(+)-2-methyl-1-[(4-methyl-5-isoquinoline) sulfonyl]-homopiperazine as a probing molecule for Rho-kinase-involved pathway," Pharmacol. Ther. 93:225-232.

Schwartz et al. (1983) "Synergistic induction of HL-60 differentiation by 1alpha, 25-dihydroxyvitamin D3 and dimethylsulfoxide (DMSO)," Proc. Am. Assoc. Cancer Res. 24:18. Abstract No. 71.

Shim et al. (2007) "Directed differentiation of human embryonic stem cells towards a pancreatic cell fate," Diabetologia. 50:1228-1238.

Stavenger et al. (2007) "Discovery of Aminofurazan-azabenzimidazoles as Inhibitors of Rho-Kinase with High Kinase Selectivity and Antihypertensive Activity," J. Med. Chem. 50:2-5.

Strickland et al. (1983) "Structure-activity relationships of a new series of retinoidal benzoic acid derivatives as measured by induction of differentiation of murine F9 teratocarcinoma cells and human HL-60 promyelocytic leukemia cells," Cancer Res. 43:5268-5272.

Suemori et al. (2006) "Efficient establishment of human embryonic stem cell lines and long-term maintenance with stable karyotype by enzymatic bulk passage," Biochem. Biophys. Res. Commun. 345:926-932.

Takahashi et al. (2006) "Induction of pluripotent stem cells from mouse embryonic and adult fibroblast cultures by defined factors," Cell. 126:663-676.

Takahashi et al. (2007) "Induction of pluripotent stem cells from adult human fibroblasts by defined factors," Cell. 131:861-872.

Takenaga et al. (1980) "Effects of retinoids on induction of differentiation of cultured mouse myeloid leukemia cells," Cancer Res. 40:914-919.

Tamura et al. (1990) "Synthetic retinoids, retinobenzoic acids, Am80, Am580 and Ch55 regulate morphogenesis in chick limb bud," Cell Differ. Dev. 32:17-26.

Thomson et al (1996) "Pluripotent cell lines derived from common marmoset (*Callithrix jacchus*) blastocysts," Biol. Reprod. 55:254-259.

Thomson et al. (1995) "Isolation of a primate embryonic stem cell line," Proc. Natl. Acad. Sci. USA. 92:7844-7848.

Thomson et al. (1998) "Embryonic stem cell lines derived from human blastocysts," Science 282:1145-1147.

Thomson et al. (1998) "Primate embryonic stem cells," Curr. Top. Dev. Biol. 38:133-165.

Jehata et al. (1997) "Calcium sensitization of smooth muscle mediated by a Rho-associated protein kinase in hypertension," Nature. 389:990-994.

Wakayama et al. (2001) "Differentiation of embryonic stem cell lines generated from adult somatic cells by nuclear transfer," Science. 292:740-743.

Wakayama et al. (2005) "Establishment of male and female nuclear transfer embryonic stem cell lines from different mouse strains and tissues," Biol. Reprod. 72:932-936.

Yu et al. (2007) "Abstract 381: Dorsomorphin, A Novel Inhibitor of Bone Morphogenetic Protein Signaling," Circulation 116:II_60.

Yu et al. (2007) "Induced pluripotent stem cell lines derived from human somatic cells," Science. 318:1917-1920.

Yu et al. (2008) "Dorsomorphin inhibits BMP signals required for embryogenesis and iron metabolism," Nat. Chem. Biol. 4:33-41.

(56) References Cited

OTHER PUBLICATIONS

Zhang et al. (2009) "Highly efficient differentiation of human ES cells and iPS cells into mature pancreatic insulin-producing cells," Cell Research. 19:429-438.
International Preliminary Report on Patentability corresponding to International Patent Application No. PCT/JP2015/064529, dated Nov. 22, 2016—provided with an English translation only.
Supplementary European Search Report corresponding to European Patent Application No. 15795700.2, dated Jan. 8, 2018.
Lindemann et al. (2003) "Interfering with TGFβ-induced Smad3 nuclear accumulation differentially affects TGFβ-dependent gene expression," Mol. Cancer 2:20. pp. 1-10.
Narumiya et al. (2000) "Use and properties of ROCK-specific inhibitor Y-27632," Methods Enzymol. 325:273-284.
Metcalfe et al. (2011) "Inhibition of GSK3 by Wnt signalling—two contrasting models," Cell Science. 124:3537-3544.
Toyoda et al. (Jan. 28, 2015) "Cell aggregation optimizes the differentiation of human ESCs and iPSCs into pancreatic bud-like progenitor cells," Stem Cell Res. 14:185-197.
International Search Report with Written Opinion corresponding to International Patent Application No. PCT/JP2015/064529, dated Aug. 25, 2015.

\* cited by examiner

A

B

Pancreatic cells derived from human ES cells
(30 days after implantation)
PDX1 insulin

METHOD FOR GENERATING PANCREATIC BUD CELLS AND THERAPEUTIC AGENT FOR PANCREATIC DISEASE CONTAINING PANCREATIC BUD CELLS

RELATED APPLICATIONS

This application is a 35U.S.C. § 371filing of International Application No. PCT/JP2015/064529, filed May 20, 2015, which claims priority to Japanese Patent Application No. 2014-105049 filed on May 21, 2014, each of which is incorporated herein by reference in its entirety.

TECHNICAL FIELD

The present invention relates to a method for generating pancreatic bud cells and a therapeutic agent for treating a pancreatic disease containing the pancreatic bud cells generated by the method. The present application further relates to a method for treating a pancreatic disease by using the pancreatic bud cells.

BACKGROUND ART

The pancreas functions as an exocrine gland which secretes digestive enzymes such as pancreatic lipase, trypsin, elastase and pancreatic amylase as well as an endocrine gland which secretes pancreatic hormones such as glucagon, insulin, somatostatin and pancreatic polypeptide (PP). Ghrelin has been known as a stomach hormone and in recent years, it has been reported that ghrelin is also secreted by cells in the pancreas. The pancreatic hormones are produced by pancreas islets that are cell cluster composed of four types of cells: α cells, β cells, δ cells and PP cells in the pancreas.

Insulin plays important roles in promoting glucose utilization, protein synthesis and production and storage of neutral fats, lowering blood glucose level as well as maintaining blood glucose within a normal range. Glucagon is a hyperglycemic hormone that functions via hepatic glycogenolysis or gluconeogenesis, and plays an important role in regulating sugar metabolism along with insulin. Somatostatin acts via a somatostatin receptor and suppresses secretion of various hormones such as glucagon and insulin in the pancreas. PP has been known as a satiety factor that is secreted from the cells in the islets of Langerhans in response to food intake, and suppresses the food intake and suppresses body weight gain. Ghrelin stimulates food intake and increases body weight by lowering fat oxidation.

Diabetes is a disease developed by insufficient secretion of insulin or insufficient response to insulin. Once it is developed, the disease is difficult to be cured completely. Diabetes is roughly classified into two types: type 1 diabetes mellitus which is an insulin-dependent diabetes, and type 2 diabetes mellitus which is a non-insulin-dependent diabetes.

Type 2 diabetes mellitus is a chronic disease begins with acquisition of insulin resistance, and is thought to be a type of diabetes whose onset mechanisms involve lifestyle habits such as obesity due to overeating or lack of exercise and stress. Type 2 diabetes mellitus is often developed in the middle-aged and elderly people, and many of patients with diabetes are affected with type 2 diabetes mellitus.

On the other hand, type 1 diabetes mellitus is a disease caused by destruction of β cells (insulin-producing cells) by, for example, autoimmune diseases and viral infections, which obstruct secretion of insulin in the body. Type 1 diabetes mellitus is mainly treated by a symptomatic therapy, i.e. by insulin administration. Pancreas transplantation or pancreatic islet transplantation is also employed so that the blood glucose level which continuously fluctuates in the body of the patient can become automatically controlled and the burden on the patients is reduced. Pancreas or pancreatic islet transplantation can effectively control the blood glucose level of the patient within the normal range. However, sufficient number of the organs that can be used for transplantation is not available. In addition, the patient who received the transplantation needs to take immunosuppressants for entire life to avoid immunorejection to a graft. Immunosuppressants may cause problems of infections or side effects.

A strategy including inducing insulin-producing cell in vitro from cells derived from a patient, and transplanting the induced cells into the patient has been proposed and studied. Insulin-producing cells can be obtained, for example, by obtaining cells from the epithelium of the pancreatic duct of a patient and differentiating the cells in vitro into insulin-producing cells.

Insulin-producing cells may also be obtained from pluripotent stem cells such as embryonic stem (ES) cells or induced pluripotent stem (iPS) cells by inducing differentiation of the cells into insulin-producing cells with an activin and retinoic acid (RA) (Patent Literature 1, and Non-Patent Literatures 1 to 5). Further, insulin-generating cells may also be generated by introducing PDX1 into pluripotent stem cells and culturing the cells (Patent Literature 2 and Patent Literature 3) as well as by culturing the pluripotent stem cells in the presence of suitably combined small molecule compounds (Patent Literature 4 and Non-Patent Literature 6). However, it has not been reported that any of the in vitro generated insulin-producing cells could successfully developed glucose responsiveness in a living body. On the other hand, it has been reported that pancreas precursor cells were generated and the cells secreted insulin depending on the glucose level when transplanted into a living body (Non-Patent Literatures 7 and 8).

CITATION LIST

Patent Literature

Patent Literature 1: Japanese Patent Publication No. 2009-225661
Patent Literature 2: U.S. Pat. No. 7,534,608
Patent Literature 3: Japanese Patent Publication No. 2006-075022
Patent Literature 4: WO 2011/081222

Non-Patent Literature

Non-Patent Literature 1: E. Kroon et al., Nature Biotechnology (2008) Vol. 26, No. 4: 443-452
Non-Patent Literature 2: K. A. D'Amour et al., Nature Biotechnology (2006) Vol. 24, No. 11: 1392-1401
Non-Patent Literature 3: W. Jiang, Cell Research (2007) 17: 333-344
Non-Patent Literature 4: J. H. Shim et al., Diabetologia (2007) 50: 1228-1238
Non-Patent Literature 5: R. Maehr et al., PNAS (2009), vol. 106, No. 37: 15768-15773
Non-Patent Literature 6: Kunisada Y et al., Stem Cell Res. (2012) vol. 8, No. 2: 274-284.
Non-Patent Literature 7: Kroon E et al., Nat Biotechnol. (2008) vol. 26, No. 4: 443-452.

Non-Patent Literature 8: Rezania A et al., Diabetes. (2012) vol. 61, No. 8: 2016-2029.

SUMMARY OF INVENTION

Technical Problem

In one aspect, an object of the present application is to provide a method for inducing differentiation from PDX1$^+$/NKX6.1$^-$ cells into pancreatic bud cells. More specifically, the object is to provide the method further including the step of inducing differentiation from pluripotent stem cells into PDX1$^+$/NKX6.1$^-$ cells and then, into pancreatic bud cells.

In another aspect, an object of the present application is to provide a therapeutic agent for treating a pancreatic disease as well as to provide a method for treating a pancreatic disease.

Solution to Problem

The inventors have conducted studies in earnest and have found, for the first time, that pancreatic bud cells can be obtained by inducing differentiation of PDX1$^+$/NKX6.1$^-$ cells by culturing the cells under a condition which causes the formation of cellular aggregates in a medium containing KGF, EGF and a BMP inhibitor. The present invention has been completed based on such findings as above.

Namely, the present invention has the following features:
[1] A method for generating pancreatic bud cells, comprising the step of culturing PDX1$^+$/NKX6.1$^-$ cells in a medium containing KGF, EGF and a BMP inhibitor.
[2] The method according to [1], wherein the medium further contains a ROCK inhibitor or a nonmuscle myosin II inhibitor.
[3] The method according to [2], wherein the ROCK inhibitor or the nonmuscle myosin II inhibitor is a compound selected from the group consisting of Y-27632, Fasudil, SR3677, GSK269962, H-1152 and Blebbistatin.
[4] The method according to [2] or [3], wherein the cells are cultured under adherent culture conditions.
[5] The method according to [1], wherein the cells are cultured under a condition which causes formation of cellular aggregates.
[6] The method according to any one of [1] to [5], wherein the PDX1$^+$/NKX6.1$^-$ cells are generated from pluripotent stem cells by a method comprising the following steps:
(1) culturing the pluripotent stem cells in a medium containing an activin; and
(2) culturing the cells obtained in step (1) in a medium containing KGF.
[7] The method according to [6], wherein the medium containing an activin used in step (1) further contains a GSK3 inhibitor.
[8] The method according to [6] or [7], wherein the medium containing KGF used in step (2) further contains a BMP inhibitor, a retinoic acid derivative and a hedgehog pathway inhibitor.
[9] The method according to any one of [1] to [8], wherein the BMP inhibitor is Noggin.
[10] The method according to any one of [7] to [9], wherein the GSK3 inhibitor is CHIR99021.
[11] The method according to any one of [8] to [10], wherein the retinoic acid derivative is TTNPB.
[12] The method according to any one of [8] to [11], wherein the hedgehog pathway inhibitor is KAAD-cyclopamine.
[13] The method according to any one of [1] to [12], wherein the pancreatic bud cells are PDX1$^+$/NKX6.1$^+$.
[14] The method according to any one of [1] to [13], wherein the pancreatic bud cells are human cells.
[15] A method for generating pancreatic bud cells from pluripotent stem cells, comprising the following steps (i) to (iii):
(i) culturing the pluripotent stem cells in a medium containing an activin;
(ii) culturing the cells obtained in step (i) in a medium containing KGF; and
(iii) dissociating the cells obtained in step (ii) into single cells and culturing the cells in a medium containing KGF, EGF and a BMP inhibitor.
[16] The method according to [15], wherein the medium used in step (iii) further contains a ROCK inhibitor or a nonmuscle myosin II inhibitor.
[17] The method according to [16], wherein the ROCK inhibitor or the nonmuscle myosin II inhibitor is a compound selected from the group consisting of Y-27632, Fasudil, SR3677, GSK269962, H-1152 and Blebbistatin.
[18] The method according to [16] or [17], wherein in step (iii), the cells obtained in step (ii) are dissociated into single cells, the dissociated cells are cultured in a medium containing KGF, a BMP inhibitor, a retinoic acid derivative and a hedgehog pathway inhibitor, and then cultured in the medium containing KGF, EGF and a BMP inhibitor.
[19] The method according to any one of [16] to [18], wherein in step (iii), the cells are cultured under adherent culture conditions.
[20] The method according to [15], wherein in step (iii), the cells are cultured under suspension culture conditions.
[21] The method according to any one of [15] to [20], wherein the medium containing an activin used in step (i) further contains a GSK3 inhibitor.
[22] The method according to any one of [15] to [21], wherein the medium containing KGF used in step (ii) further contains a BMP inhibitor, a retinoic acid derivative and a hedgehog pathway inhibitor.
[23] The method according to any one of [15] to [22], wherein the BMP inhibitor is Noggin.
[24] The method according to any one of [21] to [23], wherein the GSK3 inhibitor is CHIR99021.
[25] The method according to any one of [18] and [22] to [24], wherein the retinoic acid derivative is TTNPB.
[26] The method according to any one of [18] and [22] to [25], wherein the hedgehog pathway inhibitor is KAAD-cyclopamine.
[27] The method according to any one of [15] to [26], wherein the pancreatic bud cells are PDX1$^+$/NKX6.1$^+$.
[28] The method according to any one of [15] to [27], wherein the pancreatic bud cells are human cells.
[29] A therapeutic agent for a pancreatic disease, which comprises the pancreatic bud cells generated by the method according to any one of [1] to [28].
[30] The therapeutic agent according to [29], wherein the pancreatic disease is diabetes.
[31] The therapeutic agent according to [30], wherein the diabetes is type 1 diabetes mellitus.
[32] Use of the pancreatic bud cells generated by the method according to any one of [1] to [28], for the manufacture of a therapeutic agent for treating a pancreatic disease.
[33] Pancreatic bud cells generated by the method according to any one of [1] to [28], used for treating a pancreatic disease.
[34] A method for treating a pancreatic disease, which comprises implanting the pancreatic bud cells generated by the method according to any one of [1] to [28] to a subject in need of the treatment of the pancreatic disease.

Advantageous Effects of Invention

The present inventors have made it possible to produce pancreatic bud cells from PDX1$^+$/NKX6.1$^-$ cells, and have found for the first time that the in vivo transplanted thus produced pancreatic bud cells develop into insulin-producing cells having glucose responsiveness. The pancreatic bud cells produced by the method provided by the present application can be used for regenerative therapies for pancreatic diseases such as diabetes.

BRIEF DESCRIPTION OF DRAWINGS

FIG. 68 shows cellular aggregates at Day 12 of Stage 3 immunohistochemically stained with endocrine cell markers, INS, GCG, Somatostatin and Ghreline.

DESCRIPTION OF EMBODIMENTS

Figure 1:
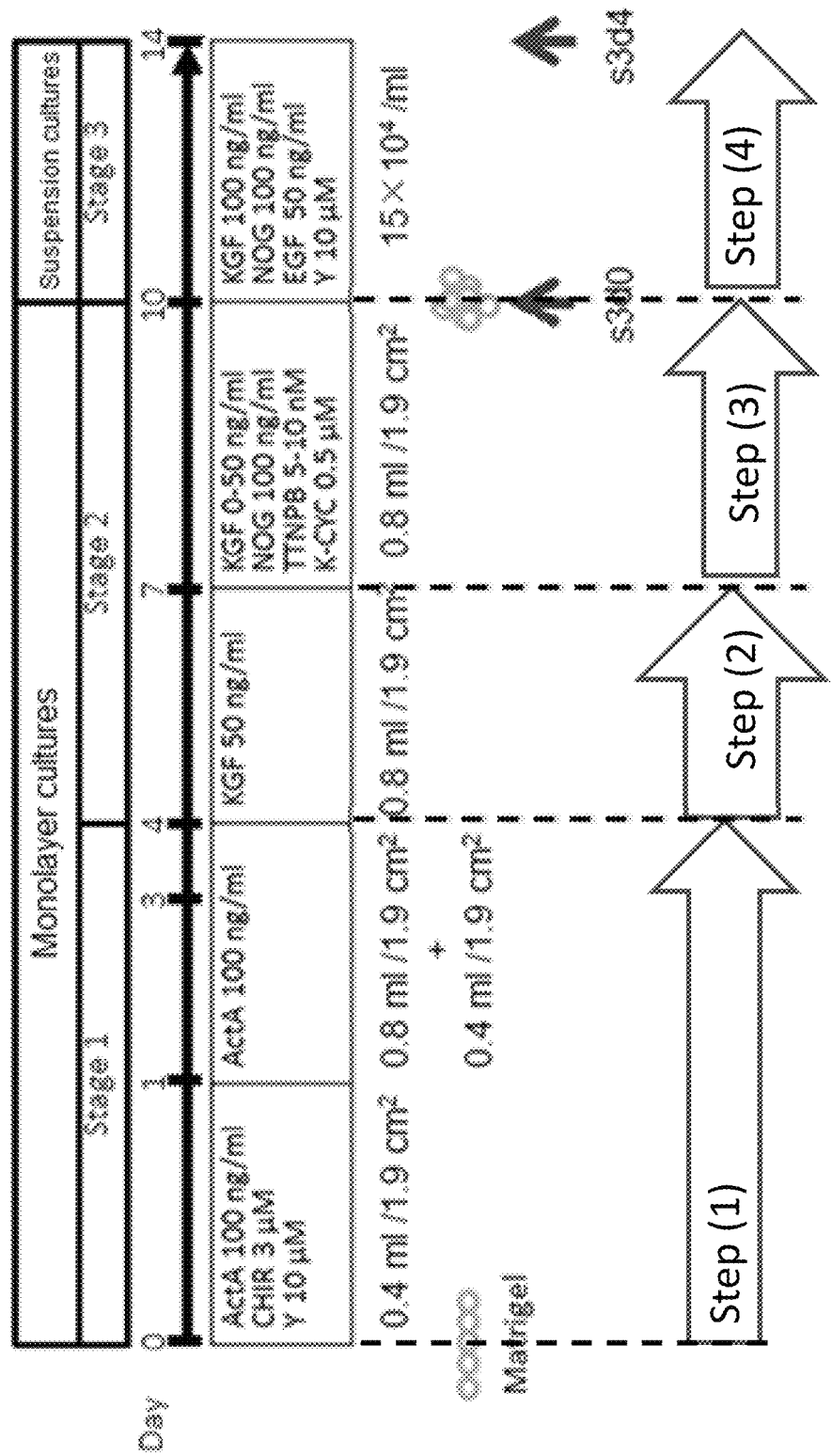
FIG. 1 shows the summary of the protocol for generating pancreatic bud cells from pluripotent stem cells.

The present application provides, in one aspect, a method for generating pancreatic bud cells, comprising the step of culturing PDX1$^+$/NKX6.1$^-$ cells in a medium containing FOE, EGF and a BMP inhibitor.

Pancreatic bud cells refer to cells which are capable of differentiating into cells which constitute the pancreas such as endocrine cells, pancreatic duct cells and exocrine cells. Examples of pancreatic bud cells include cells which express at least PDX1 and NKX6.1. The pancreatic bud cells may also express genetic markers such as SOX9 and GATA4.

The pancreatic bud cells generated according to this aspect may be provided as a cell population which also contains cells other than pancreatic bud cells, or as a purified cell population. Preferably, the cell population contains pancreatic bud cells by 30% or more, 40% or more, 50% or more, 60% or more, 70% or more, or 80% or more.

For generating pancreatic bud cells from PDX1$^+$/NKX6.1$^-$ cells, the PDX1$^+$/NKX6.1$^-$ cells may be cultured in a medium containing KGF, EGF and a BMP inhibitor under a condition which causes formation of cellular aggregates. The phrase "condition which causes formation of cellular aggregates" refers any of cell culture conditions which provide cellular aggregates in the medium. For example, cells may be substantially dissociated or decomposed from adherent culture into single cells by a conventional procedure and then, cultured in suspension cultures. Alternatively, previously generated cellular aggregates may be cultured. Preferably, cells are cultured in suspension cultures after being dissociated into single cells. By culturing dissociated single cells in suspension cultures, cells adhere to each other to form cellular aggregates. Cellular aggregates may also be formed by centrifuging the dissociated cells. Cells may be dissociated by, for example, a mechanical dissociation, or by using a dissociation solution such as a solution having protease and collagenase activities. Examples of dissociation solutions may include those containing trypsin, or trypsin and collagenase, Accutase™ and Accumax™ (Innovative Cell Technologies, Inc.)). In addition, a dissociation solution having only collagenase activity may also be used.

Suspension cultures refer to cultures in which cells are cultured in a state where the cells do not adhere to the culture dish. Suspension cultures may be performed by using, but not particularly limited to, a culture dish which has not been treated to improve cellular adhesiveness (for example, extracellular matrix coatings), or a culture dish which has been treated to suppress cellular adhesion (for example, poly-hydroxyethyl methacrylate (poly-HEMA) coating or a polymer of 2-methacryloyloxyethylphosphorylcholine (Lipidure) coating).

The size of a cellular aggregate is not particularly limited, and a cellular aggregate may be formed by at least $3\times10^3$ or more cells, and for example, by $1\times10^4$ or more, $2\times10^4$ or more, $3\times10^4$ or more, $4\times10^4$ or more and $5\times10^4$ or more cells.

In another aspect, PDX1$^+$/NKX6.1$^-$ cells are dissociated into single cells and cultured in adherent cultures. The cells are dissociated into single cells and cultured in adherent cultures in a medium used in Stage 2 described below. The time period of adherent cultures in the medium used in Stage 2 is not particularly limited, and may be one day or more, 2 days or more, and three days or more. Preferable time period is one day. The medium used in Stage 2 may comprise a ROCK inhibitor in order to suppress apoptosis of the cells after aggregates of pluripotent stem cells are dissociated into single cells. ROCK inhibitors discussed below may be used in this embodiment and preferable ROCK inhibitor is Y-27632.

In the specification and claims of the present application, adherent cultures refer to any of culturing methods wherein culture dish used for the culture is suitably coated. Examples of coating materials include Matrigel (BD Biosciences), Synthemax (Corning), gelatins, extracellular proteins, for example, collagen, laminin such as laminin-111, -411 or -511, heparan sulfate proteoglycan and entactin, fragments of the extracellular protein and combinations thereof.

The medium used for culturing PDX1$^+$/NKX6.1$^-$ cells to generate pancreatic bud cells can be prepared by adding KGF, EGF and a BMP inhibitor appropriately to a basal medium for animal cell culture. Examples of basal media include MEM Zinc Option, IMEM Zinc Option, IMDM, Medium 199, Eagle's Minimum Essential Medium (EMEM), α-MEM, Dulbecco's modified Eagle's Medium (DMEM), Ham's F12 Medium, RPMI 1640 Medium, Fischer's Medium, and mixtures of these media. The basal medium may be supplemented with serum, for example, fetal bovine serum (FBS). Alternatively, be a serum-free medium may be used. As required, the basal medium may contain, for example, one or more alternatives to sera such as albumin, transferrin, KnockOut Serum Replacement (KSR, an alternative to serum used for culturing ES cells) (Invitrogen), N2 Supplement (Invitrogen), B27 Supplement (Invitrogen), a fatty acid, insulin, a collagen precursor, a trace element, 2-mercaptoethanol and 3'-Thioglycerol, and the basal medium may contain one or more substances such as a lipid, an amino acid, L-glutamine, GlutaMAX (Invitrogen), a nonessential amino acid (NEAA), a vitamin, a growth factor, an antibiotic, an antioxidant, pyruvic acid, a buffer agent, an inorganic salt, and equivalents thereof. In one embodiment, the basal medium is IMEM Zinc Option containing B-27 Supplement.

KGF is a protein called Keratinocyte Growth. Factor and is sometimes also referred to as FGF-7. KGF is commercially available from, for example, R&D systems, Inc. The concentration of KGF may be from 1 ng/ml to 1 μg/ml, preferably from 5 ng/ml to 500 ng/ml, and more preferably from 10 ng/ml to 200 ng/ml.

EGF is a protein called epidermal growth factor. EGF is commercially available from, for example, R&D systems, Inc. The concentration of EGF may be from 1 ng/ml to 1 μg/ml, preferably from 5 ng/ml to 500 ng/ml, and more preferably from 10 ng/ml to 100 ng/ml.

Examples of the BMP inhibitors include protein inhibitors such as Chordin, Noggin and Follistatin; Dorsomorphin or 6-[4-(2-piperidin-1-yl-ethoxy)phenyl]-3-pyridin-4-yl-pyrazolo[1,5-a]pyrimidine and a derivative thereof (P. B. Yu et al. (2007), Circulation, 116: II_60, P. B. Yu et al. (2008), Nat. Chem. Biol., 4:33-41, J. Hao et al. (2008), PLoS ONE, 3 (8): e2904), and LDN-193189 or 4-(6-(4-(piperazin-1-yl)phenyl)pyrazolo[1,5-a]pyrimidin-3-yl)quinoline. Preferable BMP inhibitor is Noggin. Noggin is commercially available, for example, from Peprotech.

When Noggin is used as BMP inhibitor, the concentration of Noggin may be from 1 ng/ml to 1 µg/ml, preferably from 5 ng/ml to 500 ng/ml, and more preferably from 50 ng/ml to 200 ng/ml.

The medium used for culturing PDX1$^+$/NKX6.1$^-$ cells to generate pancreatic bud cells may further contain a ROCK inhibitor or a nonmuscle myosin II inhibitor. When the above-described PDX1$^+$/NKX6.1$^-$ cells are cultured in adherent cultures, it is preferable that the ROCK inhibitor or the nonmuscle myosin II inhibitor is further added to the medium.

The ROCK inhibitor is not particularly limited as long as it can suppress the function of Rho-kinase (ROCK), and examples of ROCK inhibitor include Y-27632 (for example, see Ishizaki et al., Mol. Pharmacol. 57, 976-983 (2000); Narumiya et al., Methods Enzymol. 325, 273-284 (2000)), Fasudil/HA1077 (Uenata et al., Nature 389: 990-994 (1997)), SR3677 (Feng Y et al., J Med Chem. 51: 6642-6645 (2008)), GSK269962 (Stavenger R A et al., J Med Chem. 50: 2-5 (2007) or WO 2005/037197), H-1152 (Sasaki et al., Pharmacol. Ther. 93: 225-232 (2002)), Wf-536 (Nakajima et al., Cancer Chemother Pharmacol. 52 (4): 319-324 (2003)) and derivatives thereof, as well as an antisense nucleic acid against ROCK, an RNA interference-inducing nucleic acid (for example, an siRNA) against ROCK, a dominant negative mutant of ROCK, and expression vectors for them. In addition, as the ROCK inhibitor, other known low molecular weight compounds may be used (U.S. patent application publications Nos. 2005/0209261, 2005/0192304, 2004/0014755, 2004/0002508, 2004/0002507, 2003/0125344 and 2003/0087919, as well as International Publications Nos. WO 2003/062227, WO 2003/059913, WO 2003/062225, WO 2002/076976, and WO 2004/039796). In the present invention, one or more kinds of ROCK inhibitors may be used. Examples of the ROCK inhibitors which are preferably used in this step include Y-27632, Fasudil/HA1077, SR3677, GSK269962 and H-1152.

When Y-27632 is used as the ROCK inhibitor, the concentration of Y-27632 in the medium may be from 0.1 µM to 100 µM, preferably from 1 µM to 500 µM, and more preferably from 10 µM to 200 µM.

When Fasudil/HA1077 is used as the ROCK inhibitor, the concentration of Fasudil/HA1077 in the medium may be from 1 µM to 100 µM, and preferably from 10 µM to 100 µM.

When SR3677 is used as the ROCK inhibitor, the concentration of SR3677 in the medium may be from 0.1 µM to 50 µM, and preferably from 0.5 µM to 50 µM.

When GSK269962 is used as the ROCK inhibitor, the concentration of GSK269962 in the medium may be from 0.001 µM to 100 µM, is preferably from 0.005 µM to 50 µM, and more preferably from 0.05 µM to 120 µM.

When H-1152 is used as the ROCK inhibitor, the concentration of H-1152 in the medium may be from 5 µM to 100 µM, and preferably from 10 µM to 50 µM.

The nonmuscle myosin II inhibitor may be an ATPase inhibitor that inhibits the ATPase activity of the heavy chain subunit of nonmuscle myosin IIA, nonmuscle myosin III which is one of heavy chain isoforms of nonmuscle myosin II or a myosin light chain kinase inhibitor. Examples of the nonmuscle myosin II inhibitors may include blebbistatin (Blebbistatin) A3, Calphostin C, Goe6976, Goe7874, Fasudil/HA1077, Hypericin, K-252a, KT5823, ML-7, ML-9, Piceatannol, Staurosporine, W-5, W-7, W-12, W-13 and Wortmannin. Preferred nonmuscle myosin II inhibitors are blebbistatin and Fasudil/HA1077.

When blebbistatin is used as the nonmuscle myosin II inhibitor, the concentration of blebbistatin in the medium may be from 1 µM to 200 µM, and preferably from 10 µM to 100 µM.

The medium used for the step of culturing PDX1$^+$/NKX6.1$^-$ cells to generate pancreatic bud cells according to the present invention may further contain a TGFβ inhibitor. The TGFβ inhibitor is a substance which inhibits the signal transduction starts from the binding of TGFβ to its receptor and leads to SMAD. The TGFβ inhibitor is not particularly limited as long as it inhibits the binding of TGF to the receptor, an ALK family protein, or inhibits phosphorylation of SMAD caused by the ALK family protein. Examples of TGF inhibitors include Lefty-1 (NCBI Accession Nos: NM 010094 (mouse), and NM_020997 (human)), SB431542 and SB202190 (R. K. Lindemann et al., Mol. Cancer, 2003, 2: 20), SB505124 (GlaxoSmithKline), NPC30345, SD093, SD908, SD208 (Scios), LY2109761, LY364947, LY580276 (Lilly Research Laboratories), A-83-01 (WO 2009/146408), ALK5 inhibitor II (2-[3-[6-methylpyridin-2-yl]-1H-pyrazol-4-yl]-1,5-naphthyridine), TGFβRI kinase inhibitor VIII (6-[2-tert-butyl-5-[6-methylpyridin-2-yl]-1H-imidazol-4-yl]-quinoxaline) and derivatives thereof. Preferably, the TGFβ inhibitor may be ALK5 inhibitor II.

When ALK5 inhibitor II is used as the TGF inhibitor, the concentration of ALK5 inhibitor II in the medium may be from 0.01 µM to 100 µM, is preferably from 0.1 µM to 50 µM, and more preferably from 1 µM to 20 µM.

The TGFβ inhibitor may preferably be added two days after the start of culturing PDX1$^+$/NKX6.1$^-$ cells. The time period of addition of the TGFβ inhibitor is not particularly limited, and may be one day or more, 2 days or more, 3 days or more, or 4 days or more.

The maximum time period of the Stage of culturing PDX1$^+$/NKX6.1$^-$ cells to generate pancreatic bud cells is not limited since culturing for a long period of time does not particularly affect the generation efficiency of pancreatic bud cells. For example, the cells in this Stage may be cultured for 4 days or more, 5 days or more, 6 days or more, 7 days or more, 8 days or more, 9 days or more, 10 days or more, 11 days or more, 12 days or more, 13 days or more, or 14 days or more. Preferably, the cells may be cultured in this Stage for 4 days or more and 20 days or less.

In the Stage of culturing PDX1$^+$/NKX6.1$^-$ cells to generate pancreatic bud cells, the cells may be cultured at a temperature from about 30° C. to about 40° C., and preferably about 37° C. In this step, the cells are cultured under a $CO_2$-containing air atmosphere, and the concentration of $CO_2$ is preferably from about 2% to about 5%.

PDX1$^+$/NKX6.1$^-$ cells are not particularly limited as long as the cells express PDX1 but do not express NKX6.1. The phrase "cells express PDX1" means that PDX1 gene or PDX1 gene product can be detected in the cells by a known method, and the phrase "cells do not express NKX6.1" means that NKX6.1 gene or NKX6.1 gene product cannot be detected by any known method. Examples of the known detection method include immunostaining.

PDX1$^+$/NKX6.1$^-$ cells may be isolated from the living body or may be generated from other types of cells such as pluripotent stem cells by a known method. In a certain embodiment, PDX1⁺/NKX6.1⁻ cells may be those generated from pluripotent stem cells by a method comprising the following stages:
(Stage 1) culturing the pluripotent stem cells in a medium containing an activin; and
(Stage 2) culturing the cells obtained in Stage 1 in a medium containing KGF.

In one embodiment, a method for generating pancreatic bud cells from pluripotent stem cells including the stage of inducing pancreatic bud cells from PDX1⁺/NKX6.1⁻ cells as Stage 3 of the above-described method is provided:
(Stage 1) culturing the pluripotent stem cells in a medium containing an activin;
(Stage 2) culturing the cells obtained in Stage 1 in a medium containing KGF; and
(Stage 3) dissociating the cells (PDX1⁺/NKX6.1⁻ cells) obtained in Stage 2 into single cells and culturing the cells in a medium containing KGF, EGF and a BMP inhibitor.

The medium used for culturing the pluripotent stem cells in a medium containing an activin (Stage 1) according to these embodiments can be prepared by adding an activin a basal medium for animal cells. Examples of the basal media include MEM Zinc Option, IMEM Zinc Option, IMDM, Medium 199, Eagle's Minimum Essential Medium (EMEM), α-MEM, Dulbecco's modified Eagle's Medium (DMEM), Ham's F12 Medium, RPMI 1640 Medium, Fischer's Medium, and mixtures of these media. The basal medium may be supplemented with serum, for example, fetal bovine serum (FBS), or the basal medium may be a serum-free medium. As required, the basal medium may contain, for example, one or more alternatives to sera such as albumin, transferrin, KnockOut Serum Replacement (KSR) (an alternative to serum used for culturing ES cells) (Invitrogen), N2 Supplement (Invitrogen), B-27 Supplement (Invitrogen), a fatty acid, insulin, a collagen precursor, a trace element, 2-mercaptoethanol and 3'-Thioglycerol, and the basal medium may contain one or more substances such as a lipid, an amino acid, L-glutamine, GlutaMAX (Invitrogen), a nonessential amino acid (NEAA), a vitamin, a growth factor, an antibiotic, an antioxidant, pyruvic acid, a buffer agent, an inorganic salt, and equivalents thereof. In one embodiment, the basal medium is RPMI 1640 medium containing B-27 Supplement.

During Stage 1 in this embodiment, single cell suspension of pluripotent stem cells may be prepared by substantially dissociating or decomposing the cellular aggregates by a conventional procedure and cultured. Alternatively, cellular aggregates of pluripotent stem cells in which cells adhere each other may be cultured. Preferably, suspension culture of single cells may be employed. Examples of the procedures for dissociating cells include mechanical dissociation, chemical dissociation using a dissociation solution such as a solution having both protease and collagenase activities such as a solution containing trypsin and collagenase, Accutase™, Accumax™ (Innovative Cell Technologies, Inc.)) or a solution having only collagenase activity. Pluripotent stem cells may be cultured in adherent cultures by using a coated culture dish.

Adherent cultures during Stage 1 of this embodiment can be performed under the same conditions as those described above.

As an activin, any activins including activin A, activin B, activin C, activin D and activin AB may be used, and activin A is preferable. In addition, as an activin, any one of activins derived from mammals such as human and mouse may be used. As the activin used for the present invention, an activin derived from the same animal as the animal from which pluripotent stem cells used for differentiation are derived is preferably used, and for example, when pluripotent stem cells derived from human are used as starting materials, an activin derived from human is preferably used. These activins are commercially available.

The concentration of the activin in the medium may be from 0.1 to 200 ng/ml, preferably from 5 to 150 ng/ml, and more preferably from 10 to 100 ng/ml.

The medium used in Stage 1 may further contain a GSK3 inhibitor and/or a ROCK inhibitor. A GSK3 inhibitor is defined as a substance which inhibits the kinase activity of GSK-3β protein such as an ability to phosphorylate β-catenin, and many GSK3 inhibitors are known. Examples of the GSK3 inhibitors include BIO (also called GSK-3β inhibitor IX; 6-bromoindirubin3'-oxime) which is a derivative of indirubin, SB216763 (3-(2,4-dichlorophenyl)-4-(1-methyl-1H-indol-3-yl)-1H-pyrrole-2,5-dione) and SB415286 (3-[(3-chloro-4-hydroxyphenyl)amino]-4-(2-nitrophenyl)-1H-pyrrole-2,5-dione) which are derivatives of maleimide, GSK-3β inhibitor VII (4-dibromoacetophenone) which is a phenyl α bromomethylketone compound, L803-mts (also called, GSK-33β peptide inhibitor; Myr-N-GKE-APPAPPQSpP-NH2) which is a cell-penetrating phosphorylated peptide and CHIR99021 (6-[2-[4-(2,4-Dichlorophenyl)-5-(4-methyl-1H-imidazol-2-yl)pyrimidin-2-ylamino]ethylamino]pyridine-3-carbonitrile) which has a high selectivity. These compounds are commercially available, for example, from Calbiochem and Biomol. These compounds may be obtained from other suppliers or may be prepared by the user himself. The GSK-3β inhibitor used for the present invention may preferably be CHIR99021.

When CHIR99021 is used, the concentration of CHIR99021 in the medium may be from 0.01 μM to 100 μM, preferably from 0.1 μM to 10 μM, and more preferably from 1 μM to 5 μM.

The GSK3 inhibitor may preferably be added at the start of culturing pluripotent stem cells. The time period for culturing the cells in the presence of the GSK3 inhibitor is not particularly limited, and may be 1 day or more, 2 days or more, or 3 days or more. Preferably, the time period is from one day to three days.

The ROCK inhibitor used in Stage 1 may be the same as one of the above-described ROCK inhibitors and may preferably be Y-27632. The ROCK inhibitor can be used in order to suppress apoptosis of the cells after the pluripotent stem cells are dissociated into single cells. The time period for culturing the cells in the presence of the ROCK inhibitor is not particularly limited, and may be 1 day or more, or 2 days or more, and preferably, 1 day.

There is no particular upper limit of the period of Stage 1. Longer period of culture does not particularly affect the efficiency for generating pancreatic bud cells. The period of Stage 1 may be 3 days or more, 4 days or more, 5 days or more, 6 days or more, or 7 days or more. Preferably, Stage 1 may be 4 days.

In Stage 2, the medium used for culturing the cells obtained in Stage 1 may be prepared by adding KGF to a basal medium for animal cells. Examples of the basal media may include MEM Zinc Option, IMEM Zinc Option, IMDM, Medium 199, Eagle's Minimum Essential Medium (EMEM), α-MEM, Dulbecco's modified Eagle's Medium (DMEM), Ham's F12 Medium, RPMI 1640 Medium, Fischer's Medium, and mixtures of these media. The basal medium may contain serum (for example, fetal bovine serum (FBS)) or the basal medium may be a serum-free medium. As required, the basal medium may contain, for example, one or more alternatives to sera such as albumin, transferrin, KnockOut Serum Replacement (KSR) (an alternative to serum used for culturing ES cells) (Invitrogen), N2 Supplement (Invitrogen), B-27 Supplement (Invitrogen), a fatty acid, insulin, a collagen precursor, a trace element, 2-mercaptoethanol and 3'-Thioglycerol, and the basal medium may contain one or more substances such as a lipid, an amino acid, L-glutamine, GlutaMAX (Invitrogen), a nonessential amino acid (NEAA), a vitamin, a growth factor, an antibiotic, an antioxidant, pyruvic acid, a buffer agent, an inorganic salt, and equivalents thereof. In one embodiment, the basal medium is IMEM Zinc Option containing B-27 Supplement.

KGF used in Stage 2 may be the same as the above-described KGF. The concentration of KGF in Stage 2 may preferably be lower than the above-described concentration, and for example, the concentration of KGF in Stage 2 may be from 1 ng/ml to 500 ng/ml, and preferably from 10 ng/ml to 100 ng/ml.

The medium used in Stage 2 may further contain a BMP inhibitor, a retinoic acid derivative and a hedgehog pathway inhibitor.

The BMP inhibitor used in Stage 2 may be used under the same conditions to those described above.

The retinoic acid derivative used in Stage 2 covers an artificially modified retinoic acid which retains the functions of natural retinoic acid, and examples may include 4-[[(5,6,7,8-tetrahydro-5,5,8,8-tetramethyl-2-naphthalenyl)carbonyl]amino]-Benzoic acid (AM580) (Tamura K, et al., Cell Differ. Dev. 32: 17-26 (1990)), 4-[(1E)-2-(5,6,7,8-tetrahydro-5,5,8,8-tetramethyl-2-naphthalenyl)-1-propen-1-yl]-Benzoic acid (TTNPB) (Strickland S, et al., Cancer Res. 43: 5268-5272 (1983)), retinol palmitate, retinol, retinal, 3-dehydroretinoic acid, 3-dehydroretinol, 3-dehydroretinal, and compounds described in Abe, E., et al., Proc. Natl. Acad. Sci. (USA) 78: 4990-4994 (1981), Schwartz, E. L. et al., Proc. Am. Assoc. Cancer Res. 24: 18 (1983), and Tanenaga, K. et al., Cancer Res. 40: 914-919 (1980). Examples of the retinoic acid derivative preferably used in this Stage include TTNPB. The concentration of the retinoic acid derivative used in this Stage can be appropriately selected by those skilled in the art depending on the retinoic acid derivative used. When TTNPB is used, its concentration in the medium may be from 1 nM to 100 nM, preferably from 5 nM to 50 nM, and more preferably from 5 nM to 10 nM.

The hedgehog pathway inhibitor used in Stage 2 means a substance which inhibits signals, such as Smoothened, elicited by the binding of any one of Sonic Hedgehog, Indian hedgehog and Desert Hedgehog to their membrane receptor, Patched. The hedgehog pathway inhibitor may be any substance that inhibits signals elicited by the binding of a Hedgehog to its receptor. Examples of the hedgehog pathway inhibitor include cyclopamine, jervine, 3-Keto-N-(aminoethyl-aminocaproyl-dihydro-cinnamoyl) (KAAD)-cyclopamine, CUR-61414, SANT-1, SANT-2, SANT-3, SANT-4, IPI-926, IPI-269609, GDC-0449 and NVP-LDE-225. Preferably, the hedgehog pathway inhibitor is KAAD-cyclopamine. The concentration of the hedgehog pathway inhibitor used in Stage can be appropriately selected by those skilled in the art depending on the hedgehog pathway inhibitor used. When KAAD-cyclopamine is used, its concentration in the medium may be from 0.1 nM to 1 µM, and preferably from 1 nM to 500 nM.

In the specification and claims of the present application, pluripotent stem cells refer to stem cells which have pluripotency, that is the ability of cells to differentiate into all type of the cells in the living body, as well as proliferative capacity. Examples of the pluripotent stem cells include embryonic stem (ES) cells (J. A. Thomson et al. (1998), Science 282: 1145-1147; J. A. Thomson et al. (1995), Proc. Natl. Acad. Sci. USA, 92: 7844-7848; J. A. Thomson et al. (1996), Biol. Reprod., 55: 254-259; J. A. Thomson and V. S. Marshall (1998), Curr. Top. Dev. Biol., 38: 133-165), nuclear transfer embryonic stem (ntES) cells that can be obtained by nuclear transplantation into the ES cells (T. Wakayama et al. (2001), Science, 292: 740-743; S. Wakayama et al. (2005), Biol. Reprod., 72: 932-936; J. Byrne et al. (2007), Nature, 450: 497-502), germline stem cells ("GS cells") (M. Kanatsu-Shinohara et al. (2003) Biol. Reprod., 69: 612-616; K. Shinohara et al. (2004), Cell, 119: 1001-1012), embryonic germ cells ("EG cells") (Y. Matsui et al. (1992), Cell, 70: 841-847; J. L. Resnick et al. (1992), Nature, 359: 550-551), induced pluripotent stem (iPS) cells (K. Takahashi and S. Yamanaka (2006) Cell, 126: 663-676; K. Takahashi et al. (2007), Cell, 131:861-872; J. Yu et al. (2007), Science, 318: 1917-1920; Nakagawa, M. et al., Nat. Biotechnol. 26: 101-106 (2008); WO 2007/069666), pluripotent cells derived from cultured fibroblasts and bone marrow stem cells (Multi-lineage differentiating Stress Enduring cells, Muse cells) (WO 2011/007900). More preferably, the pluripotent stem cells are human pluripotent stem cells.

The iPS cells are particularly preferable as pluripotent stem cells for generating pancreatic bud cells used for implantation. For therapeutic use, it is desirable that the iPS cells are those induced from somatic cells of an individual who has the same or substantially the same HLA genotypes as those of the individual who receives implantation of the cells, from the viewpoint that the cells do not cause rejection reaction. In this regard, the phrase "substantially the same HLA" means HLAs between the donner and the recipient match to a degree that the immunoreaction against the implanted cells can be suppressed by an immunosuppressant. For example, substantially the same HLA may cover three genes match, i.e. HLA-A, HLA-B, and HLA-DR match or four genes match, i.e. HLA-A, HLA-B, HLA-DR and HLA-C mach.

In another embodiment, pancreatic bud cells obtained through the above-described procedures may be used as a medicament, in particular, for cellular therapy. The cells may be, before being administered, irradiated with radiation or treated with a compound which suppresses proliferation of the cells such as mitomycin C.

The pancreatic bud cells may be suspended in physiological saline or the like and the suspension may be administered directly to the pancreas, the mesenterium, the spleen, the liver or the kidney, in particular into the kidney subcapsule of the patient. Alternatively, the cells may be encapsulated with polyvinyl alcohol (PVA) (Qi Z et al., Cell Transplant. 21: 525-534 (2012)) or alginic acid (Dufrane D, et al., Transplantation 90: 1054-1062 (2010)) and the capsule may be administered. The cells may be administered in combination with a scaffolding material such as polyethylene glycol, gelatin, or collagen. The number of the cells administered may be appropriately determined depending on the body size, and may be, for example, from $1 \times 10^8$ to $1 \times 10^{10}$ cells/body, is preferably from $5 \times 10^8$ to $1 \times 10^{10}$ cells/body, and more preferably from $1 \times 10^9$ to $1 \times 10^{10}$ cells/body.

The pancreatic bud cells may be used for treating a pancreatic disease. Examples of the pancreatic diseases include acute pancreatitis, chronic pancreatitis, diabetes, pancreatic cancer and islet of Langerhans tumor. The pancreatic bud cells according to the present invention are induced to be insulin-producing cells which secrete insulin in response to glucose level in the body and are effective for treating diabetes. In particular, the medicament containing the pancreatic bud cells are effective for treating type 1 diabetes mellitus in which insulin-producing cells die.

The origin of the cells described in the specification are not particularly limited and may include human and non-human animals, for example, mice, rats, cattle, horses, pigs, sheep, monkeys, dogs, cats and birds. Human cells are preferably used.

The present invention is described in more detail referring to following Examples. The present invention, however, is not limited by those Examples in any way.

EXAMPLE 1

Induction of Differentiation into Pancreatic Bud Cells

Human ES cell line KhES3 gifted from Kyoto University was used. Cells were cultured according to a conventional procedure (H. Suemori et al. (2006), Biochem. Biophys. Res. Commun., 345:926-932). (Alternatively, the cells were cultured in Essential 8 Medium by using Corning Synthemax under feeder-free conditions). The KhES3 cells were induced into pancreatic bud cells according to the protocol shown in FIG. 1. An about 70% confluent culture of human ES cell line KhES3 in a culture dish was used. The cells were detached from the culture dish with CTK solution (ReproCELL Inc.) and then, dissociated into single cells with Accutase (Innovative Cell Technologies). Thus obtained single cells were seeded on well- or 6 well-plate (Greiner) coated with Matrigel (BD Biosciences) at a density of $2.0 \times 10^5$ cells/well to $3.0 \times 10^5$ cells/well. Then, the cells were induced to differentiate into pancreatic bud cells according to the following procedures.
(Stage 1)
The cells were exposed to RPMI 1640 Medium (Nacalai Tesque, Inc.) (0.4 ml/well) supplemented with 2% B-27 (Life Technologies), 100 ng/ml of activin A (R&D systems), 3 µM of CHIR99021 (Axon Medchem) and 10 µM of Y-27632 (Wako Pure Chemical Industries, Ltd.) for one day. The medium was exchanged with RPMI 1640 Medium (0.8 ml/well) supplemented with 100 ng/ml of activin A and 2% 8-27 (Life Technologies), and the cells were cultured for two days. The medium was exchanged with RPMI 1640 Medium (0.4 ml/well) supplemented with 100 ng/ml of activin A and 2% B-27 (Life Technologies), and the cells were cultured for one another day.
(Stage 2)
The cells were treated with Improved MEM Zinc Option (Invitrogen) (0.8 ml/well) containing 50 ng/ml of KGF (R&D systems) and 1% B-27 (Life Technologies) for three days. The medium was exchanged with Improved MEM Zinc Option (0.8 ml/well) containing 0-50 ng/ml of KGF, 100 ng/ml of Noggin (Peprotech), 5 nM or 10 nM of TTNPB (Santa Cruz Biotechnology), 0.5 µM of 3-Keto-N-aminoethyl-N'-aminocaproyldihydrocinnamoyl Cyclopamine (KAAD-cyclopamine or K-CYC) (Toronto Research Chemicals) and 1% B-27, and the cells were cultured for three days.
(Stage 3)
The cells obtained in Stage 2 were dissociated into single cells with trypsin and seeded on a Low Attachment 96-well plate (Lipidure Coat, NOF) at a density of $3.0 \times 10^3$ to $3.0 \times 10^4$ cells/well. Improved MEM Zinc Option ($15 \times 10^4$ cells/ml) containing 100 ng/ml of KGF, 100 ng/ml of Noggin, 50 ng/ml of EGF (R&D systems), 10 µM of Y-27632 and 1% B-27 was added to the plate, and the cells were further cultured for 4 to 20 days. During this time period, the medium was exchanged with fresh medium every 4 days. As a control, cells obtained in Stage 2 were dissociated into single cells with trypsin and seeded on a Matrigel coated 24 well plate (Greiner) at a density of $6.0 \times 10^4$ to $4.8 \times 10^5$ cells/cm$^2$ and cultured under adhesive conditions in the same medium for four days. As another control, cells obtained in Stage 2 were not dissociated, the medium was exchanged with the same medium as above, and cultured for four days.

Figure 2:
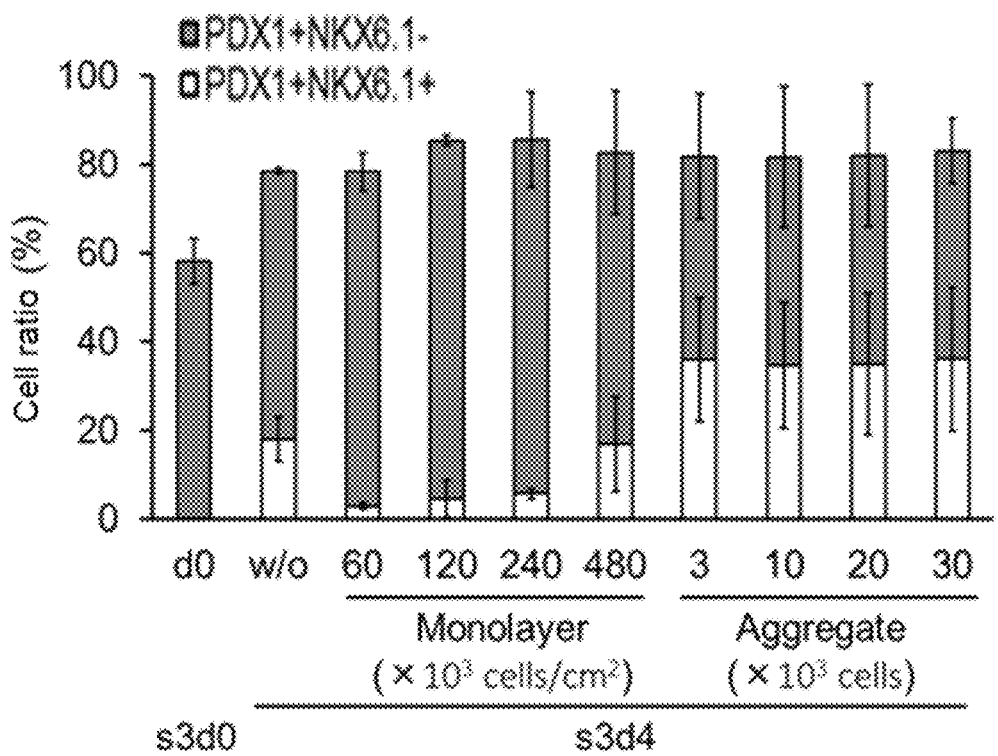
FIG. 2 shows the ratio of PDX1$^+$/NKX6.1$^-$ cells and PDX1$^+$/NKX6.1$^+$ cells in the cells obtained by each of the induction procedures. In the figure, "d0" represents cells at the end of Stage 2, "W/O" represents cells on Day 4 which were not subjected to decomposition but were only subjected to exchange of medium during Stage 3, "Monolayer" represents cells on Day 4 which were subjected to adherent culture during Stage 3 and "Aggregate" represents cells on Day 4 which were subjected to suspension cultures during Stage 3. (N=3-4)

The cells obtained at four days after the start of Stage (S3d4) were treated with BD Cytofix/Cytoperm™ Kit, stained with an anti-PDX1 antibody (R&D systems) and an anti-NKX6.1 antibody (University of Iowa), and the ratio of PDX1$^+$ cells as well as the ratio of PDX1$^+$NKX6.1$^+$ cells were determined by using a flow cytometer. The ratio of PDX1$^+$NKX6.1$^+$ cells increased (FIG. 2) in the cell aggregate obtained by culturing single cells at Stage 3. In addition, it was confirmed that a cell aggregate was sufficiently constituted by $3.0 \times 10^3$ or more cells.

EXAMPLE 2

Examination Using Various iPS Cell Lines

Four induced pluripotent stem (iPS) cell lines 585A1, 604B1, 692D2 and 648B1 established from peripheral blood mononuclear cells, (all described in Okita K, et al, Stem Cells. 2013 31: 458-466)) as well as an iPS cell line 409B2 established from fibroblast (Okita K, et al, Nat Methods. 2011 8: 409-412) are available from Center for iPS Cell Research and Application, Kyoto University. These iPS cell lines were obtained from Kyoto University and the cells were induced to differentiate into pancreatic bud cells according to the same procedures as described above.

Figure 3:
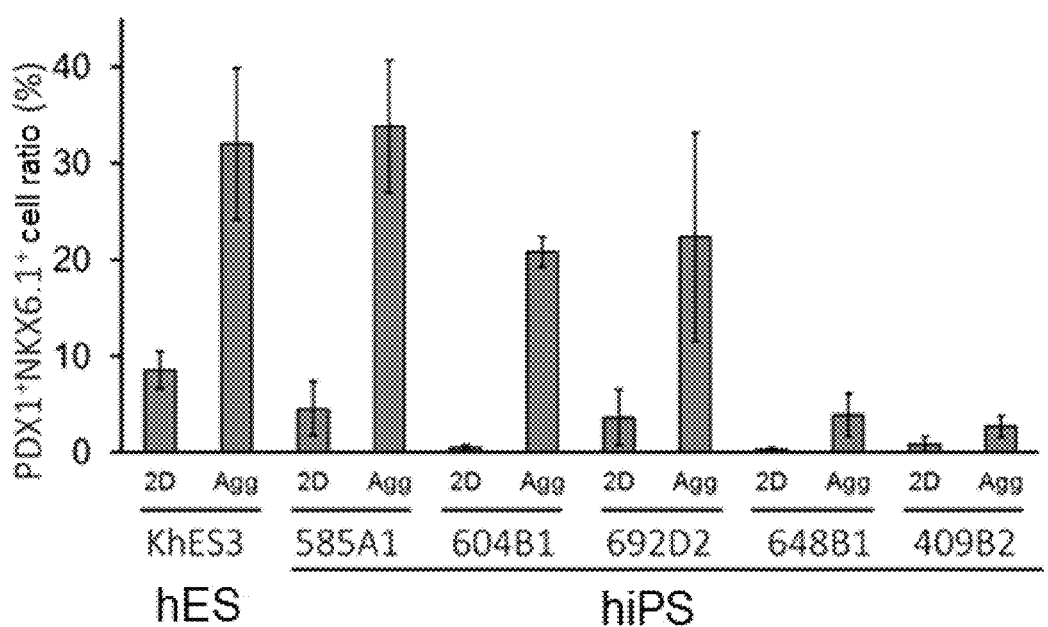
FIG. 3 shows the ratio of PDX1$^+$/NKX6.1$^+$ cells in the cells differentiated from each of pluripotent stem cell lines (KhES3, 585A1, 604B1, 692D2, 648B1 and 40952). In the figure, "2D" represents the case where adherent culture was performed during Stage 3, and "Agg" represents the case where suspension culture was performed during Stage 3. (Mean±S.D., n=3)

As a result, a higher ratio of PDX1$^+$NKX6.1$^+$ cells was obtained in the group where the cells were cultured under a condition which caused formation of cellular aggregates (Agg) than where the cells were cultured in adherent cultures (2D) during Stage 3, in all types of iPS cell lines used as starting materials (FIG. 3).

EXAMPLE 3

Study on Time Period for Culture

Figure 4:
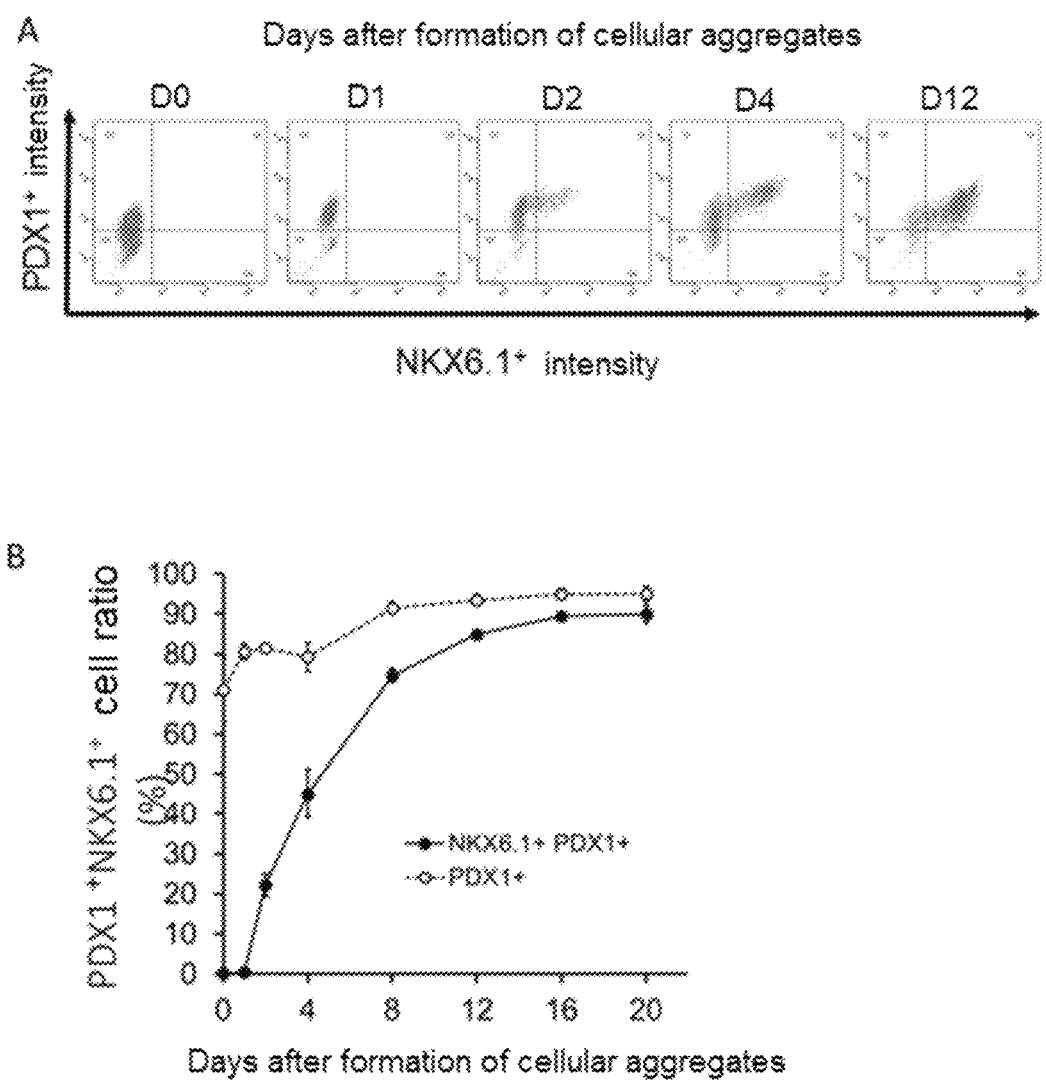
FIG. 4A shows expression intensities of PDX1 and NKX6.1 in the cells measured by using a flow cytometer at each of days 0, 1, 2, 4 and 12 of Stage 3.
FIG. 4B shows the ratio of PDX1$^+$/NKX6.1$^+$ cells at each of days 0, 4, 8, 12, 16 and 20 of Stage 3. (Mean±S.D., n=3)

A human ES cell line KhES3 was used. In Stage 3, cells were cultured for 0 day (S3d0), 1 day (S3d1), 2 days (S3d2), 4 days (S3d4), 8 days (S3d8), 12 days (S3d12), 16 days (S3d16) or 20 days (S3d20). In the cell culture obtained by culturing the cells in Stage 3 for 8 days or more, the ratio of PDX1$^+$NKX6.1$^+$ cells increased. In this examination, the ratio of PDX1$^+$NKX6.1$^+$ cells was highest at around day 12 of Stage 3. Further culture of the cells did not significantly decrease the efficiency (FIGS. 4A and 4B).

Figure 5:
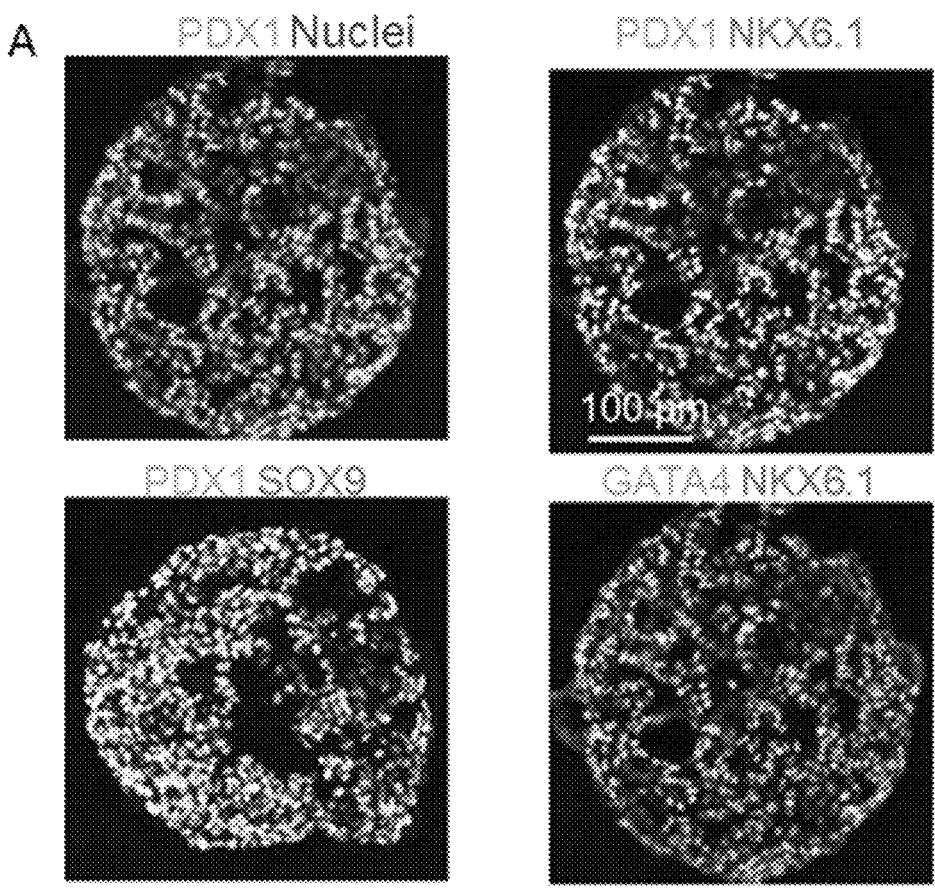
FIG. 5A shows cellular aggregates at Day 4 of Stage 3, immunohistochemically stained with pancreatic bud cell makers, PDX1, NKX6.1, SOX9 and GATA4.
FIG. 5B shows cellular aggregates at Day 4 of Stage 3, immunohistochemically stained with endocrine cell markers, INS, GCG, Somatostatin and Ghrelin.
Figure 5:
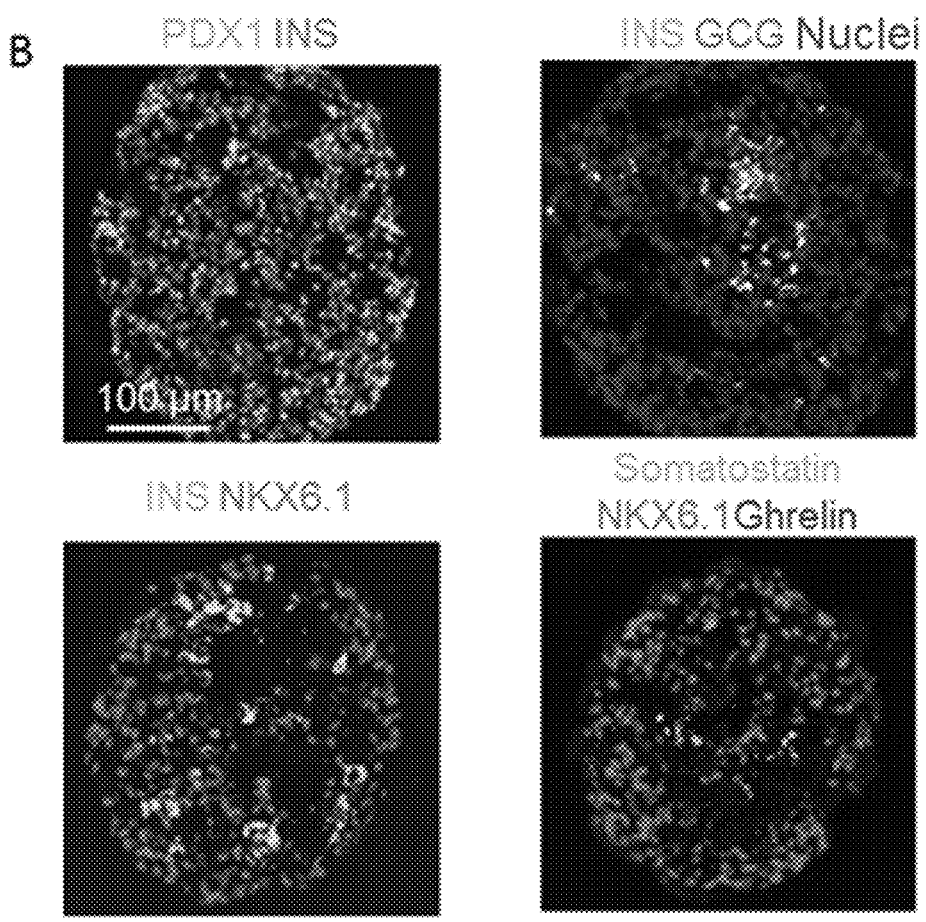
Figure 6:
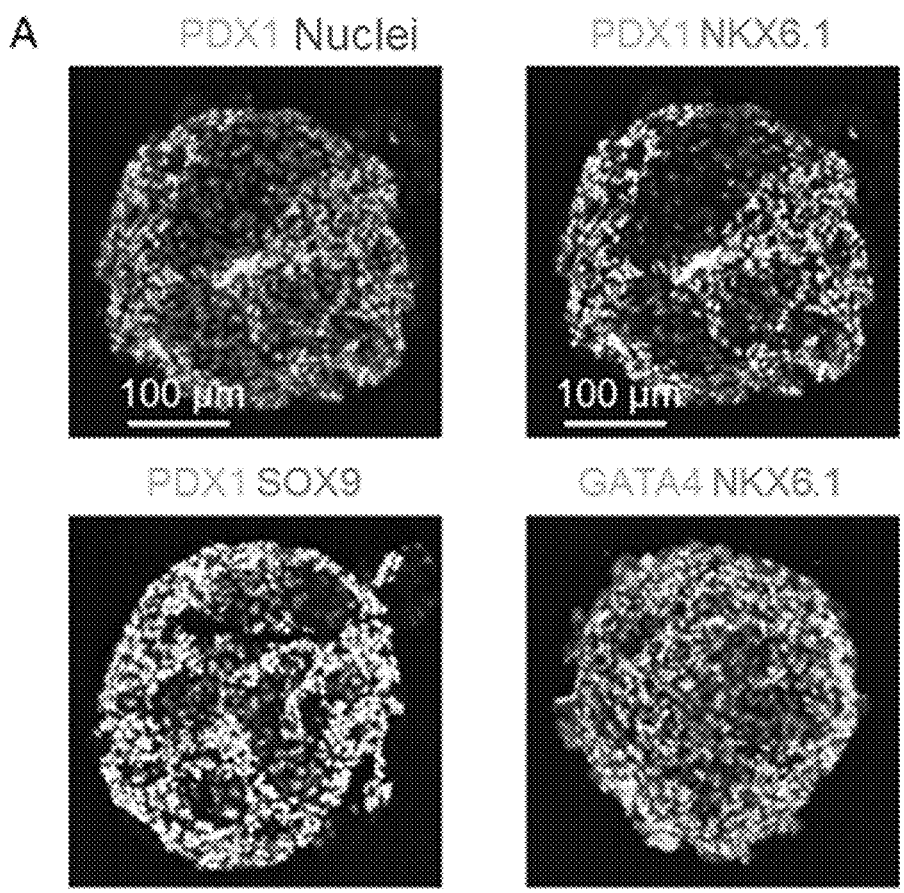
FIG. 6A shows cellular aggregates at Day 12 of Stage 3, the aggregates were immunohistochemically stained with pancreatic bud cell markers, PDX1, NKX6.1, SOX9 and GATA4.
Figure 6:
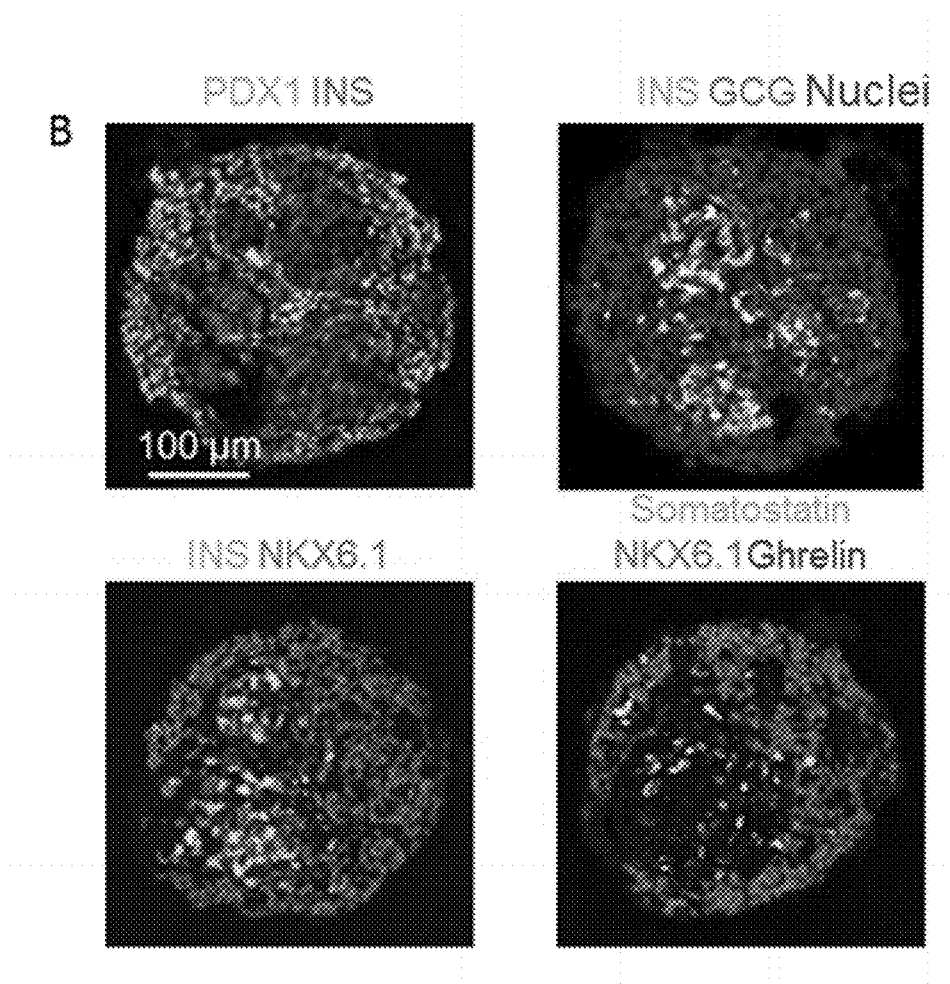

Cellular aggregates were formed from human ES cell line KhES3. Stage 3 was started with $3.0 \times 10^4$ cells/well and the cells were cultured for 4 days (S3d4) or 12 days (S3d12). Then, the cellular aggregates were subjected to immunostaining with antibodies against markers for pancreatic bud cells (PDX1, NKX6.1, SOX9 and GATA4) and those against markers for endocrine cells (INS, GCG, Somatostatin and Ghrelin) (FIG. 5 and FIG. 6). On day 12 after starting the formation of cellular aggregates (S3d12), cells expressing markers for pancreatic bud cells increased and a lot of cells expressing markers for endocrine cells appeared.

Figure 7:
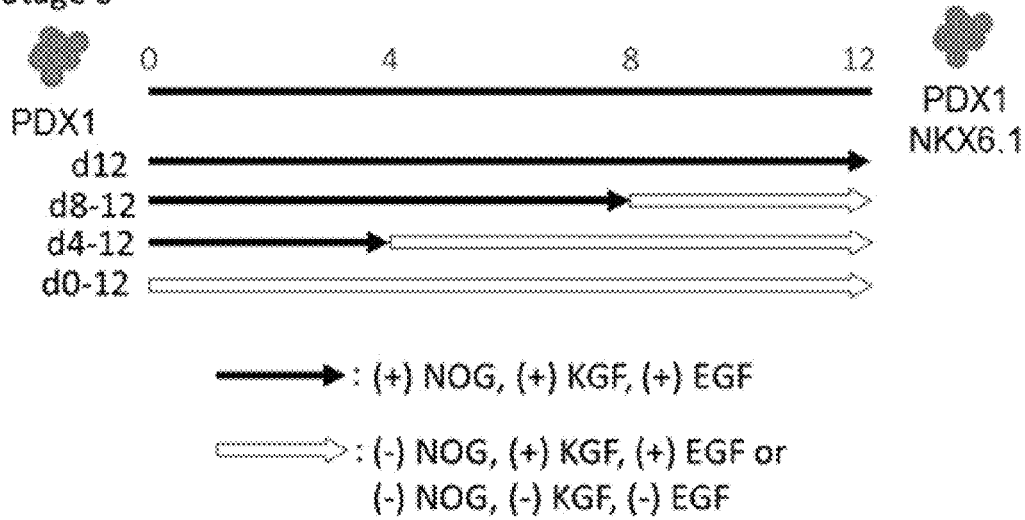
FIG. 7A shows the shows the summary of the protocol for determining culture conditions during Stage 3. In the figure, black arrows indicate conditions under which Noggin (NOG), KGF and EGF are added to the culture medium and white arrows indicate conditions under which Noggin (NOG) is not added to the culture medium or conditions under which none of Noggin (NOG), KGF and EGF is added to the culture medium.
FIG. 7B shows the ratio of PDX1$^+$/NKX6.1$^-$ cells and PDX1$^+$/NKX6.1$^+$ cells in the cells obtained under each condition.
Figure 7:
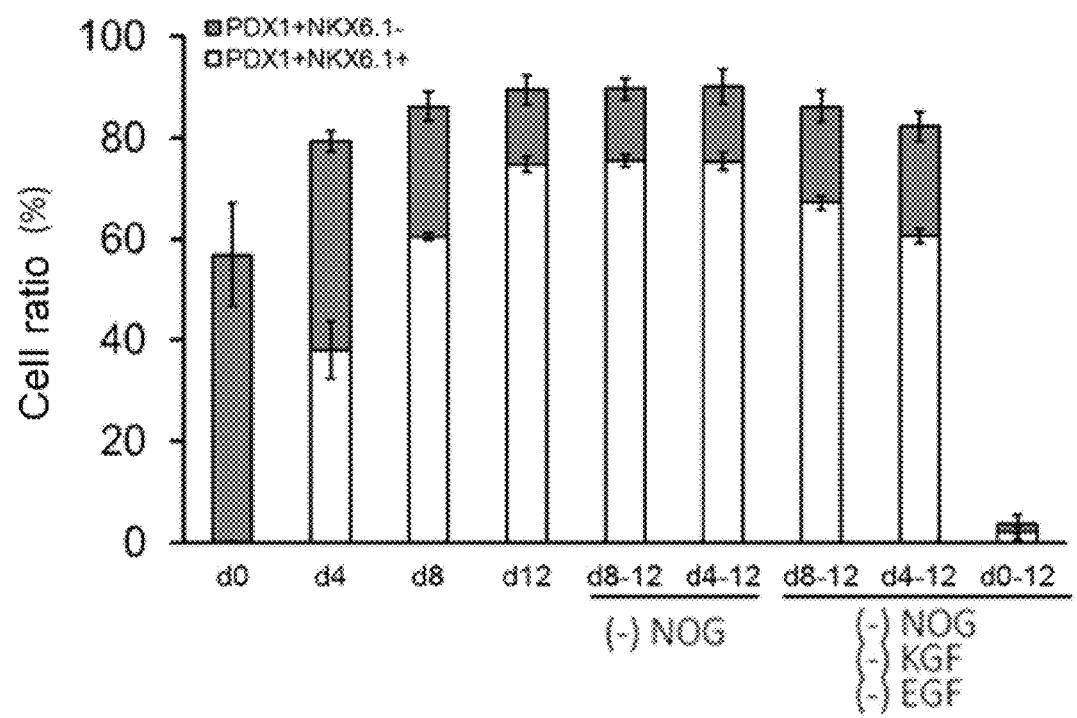

On day 4 of Stage 3, the cells were cultured in Improved MEM Zinc Option containing 1% B-27 ($15 \times 10^4$ cells/ml) or in Improved MEM Zinc Option containing 100 ng/ml of KGF, 50 ng/ml of EGF (R&D systems) and 1% B-27 ($15 \times 10^4$ cells/ml). In either case, the ratio of PDX1$^+$ NKX6.1+ cells was higher on day 12 than day 4 of Stage 3 (FIG. 7B). It has been concluded that the cell destiny is decided by culturing the cells for 4 or more days in Stage 3. Accordingly, it is desirable that Stage 3 is performed for at least 4 days.

Study of the Effect of ALK5 Inhibitor II

Figure 8:
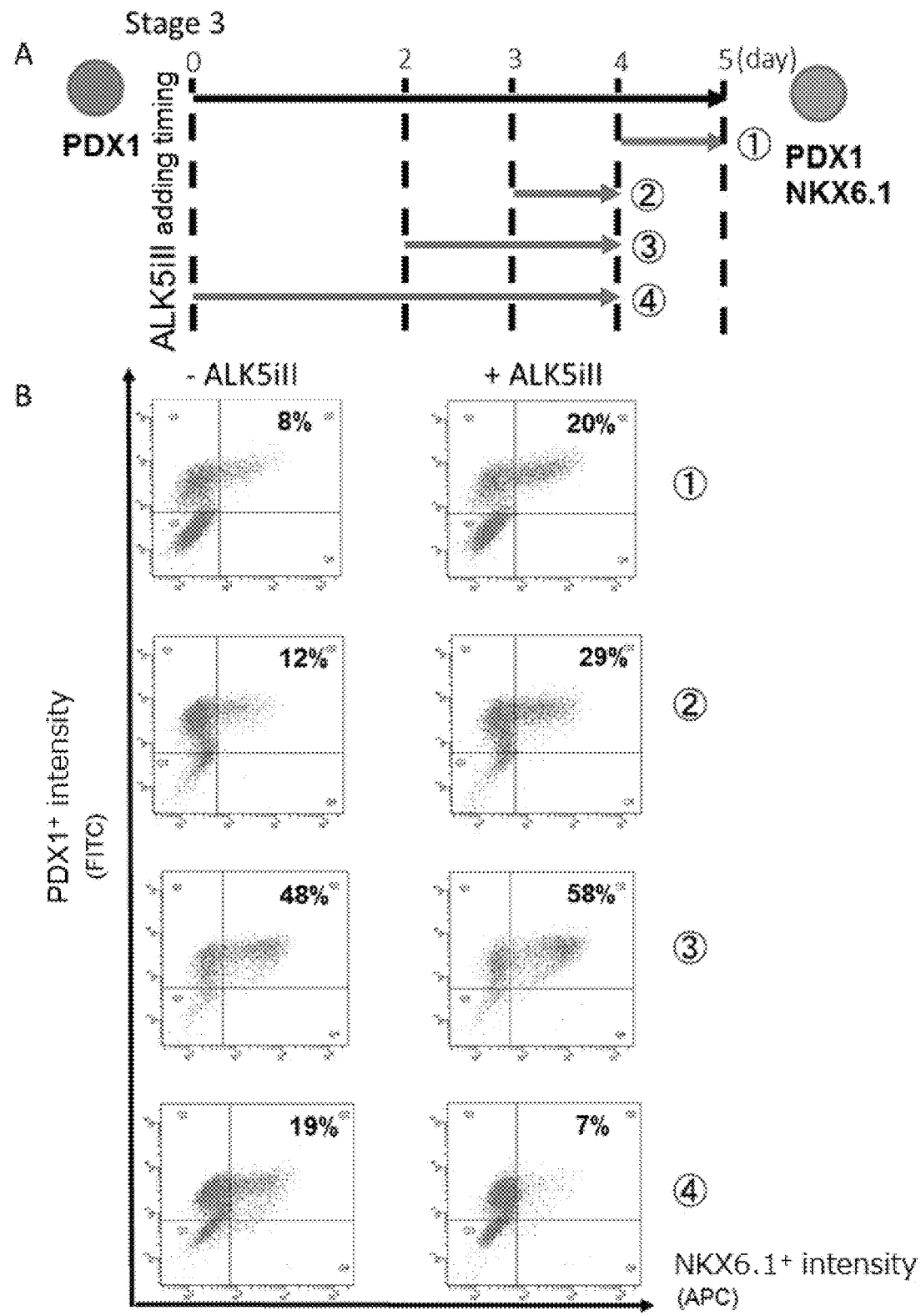
FIG. 8A shows the shows the summary of the protocol for determining effects of ALK5 inhibitor II during Stage 3. In the figure, arrows indicate time periods when ALK5 inhibitor II was added to the medium.
FIG. 8B shows expressions of PDX1 (vertical axes) and NKX6.1 (horizontal axes) under the condition where ALK5 inhibitor II was not added (the left hand in the figure) as well a s under the condition where ALK5 inhibitor II was added (the right hand in the figure). The expressions were measured by a flow cytometer. In the figure, numbers indicate the ratio of PDX1$^+$ and NKX6.1$^+$ cells contained in the culture.

The addition of ALK5 inhibitor II (Santa Cruz) in Stage 3 on day 2 or after for 1-2 days increased the ratio of PDX1+NKX6.1+ cells (FIG. 8B) (FIG. 8A).

EXAMPLE 4

Evaluation of Pancreatic Bud Cells

Figure 9:
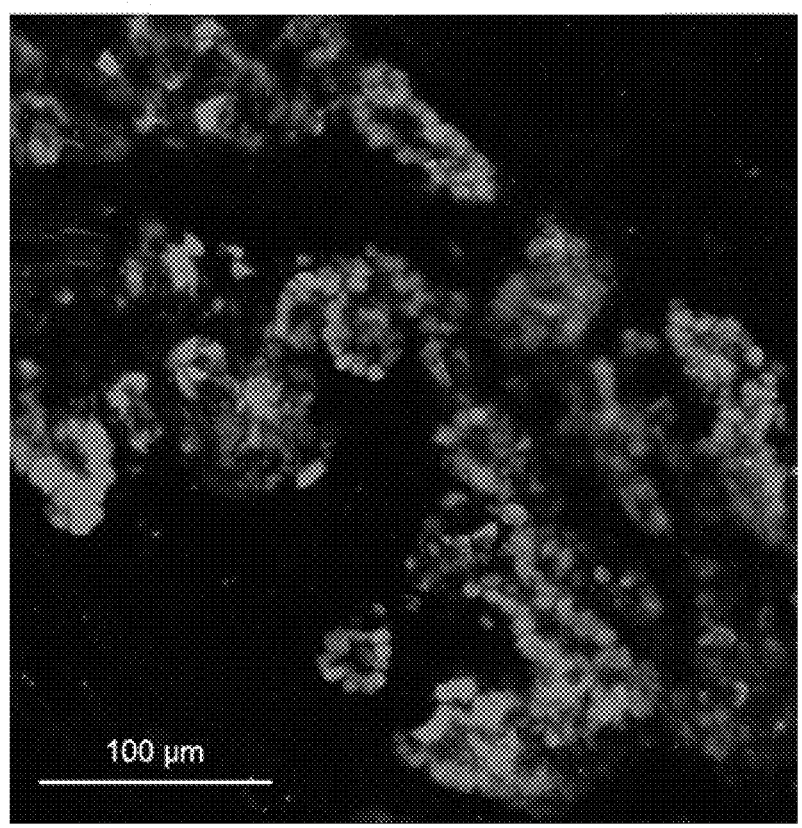
FIG. 9 shows the epididymal fat pads of an immunodeficient mouse (NOD. CB17-Prkdc$^{scid}$/J) at 30 days after the induced pancreatic bud cells were implanted. The place where the cells were implanted was immunohistochemically stained with PDX and insulin.

Cellular aggregates on day 12 of Stage 3 were collected and were implanted into the adipose tissues surrounding epididymis of an immunodeficient mouse (NOD. CB17-Prkdc$^{scid}$/J) (Charles River). Thirty days after the implantation, the implanted tissue was collected. In the obtained tissue, insulin positive cell clusters were generated adjacent to PDX1+ cells which formed tubular structures. It was confirmed that the induced pancreatic bud cells formed structures reminiscent of pancreatic epithelia in vivo (FIG. 9).

EXAMPLE 5

Therapeutic Effects of the Induced Pancreatic Bud Cells

Cellular aggregates on day 4, 5 or 12 of Stage 3 were collected and washed with physiological saline to prepare concentrates of cellular aggregates from which the medium was removed or concentrates of cellular aggregates from which the culture supernatant was removed.

Besides these, cellular aggregates on day 4 of Stage 3 were collected, and added with Improved MEM Zinc Option supplemented with 1% B-27 and 5 μM of ALES inhibitor II (Santa Cruz) to give 15×10$^4$ cells/ml suspension and cultured for one day. Then, cultured cells were washed with physiological saline to prepare concentrates of cellular aggregates from which the medium was removed or concentrates of cellular aggregates from which the culture supernatant was removed.

The obtained concentrates of cellular aggregates were implanted into the kidney subcapsule of immunodeficient mice (NOD. CB17-Prkdc$^{scid}$/J).

Figure 10:
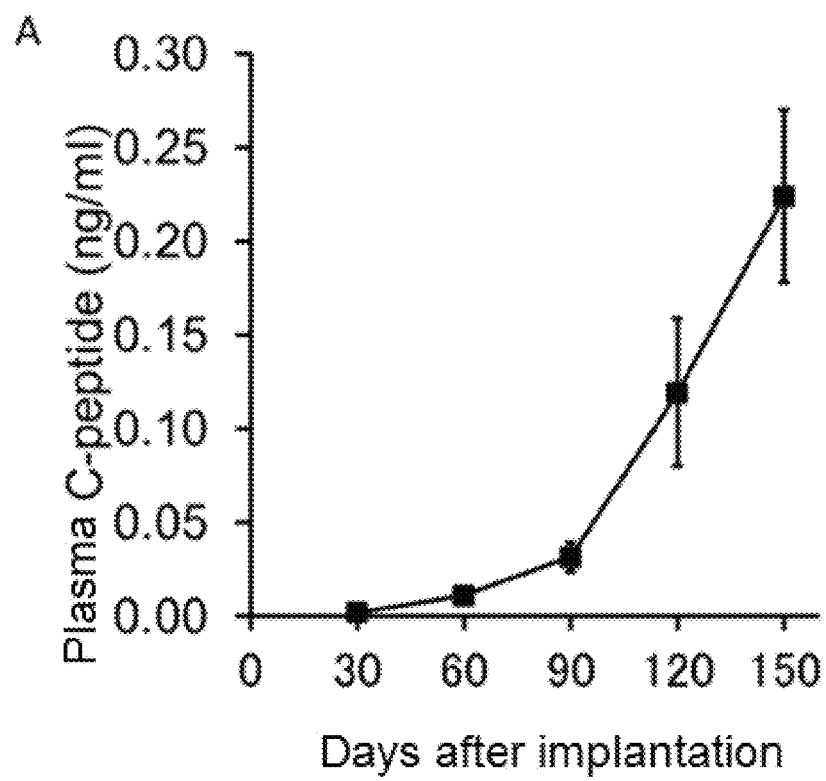
FIG. 10A shows plasma human C-Peptide levels in immunodeficient mice that received kidney subcapsular implantation of the induced pancreatic bud cells. The results are plotted to days after implantation.
FIG. 10B shows the change of plasma human C-Peptide levels caused by glucose challenges (+) in mice to which the induced pancreatic bud cells were implanted.
Figure 10:
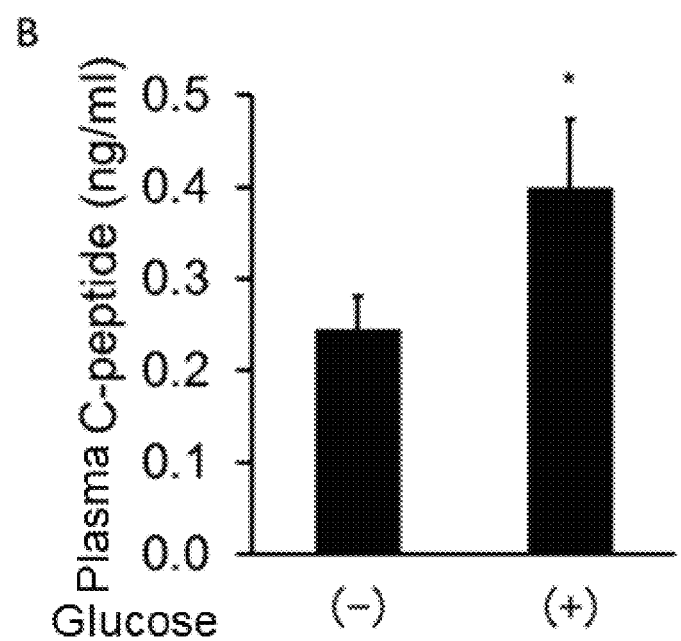

The peripheral blood was collected from the implanted mice at 150 days after the kidney subcapsular implantation of pancreatic bud cells, and the plasma human C-Peptide levels were measured with an ELISA kit (Mercodia). Human C-Peptide was confirmed in 13 out of 14 mice. Each of the concentrated cellular aggregates prepared by above-described procedures were implanted and at 150 days after the implantation, peripheral blood human C-Peptide was determined. In all concentrated cellular aggregates examined, Human C-Peptide was confirmed in the mouse plasma after 150 days from the implantation into the kidney. The level of C-Peptide increased with time from 30 days after implantation to 150 days after implantation (FIG. 10A).

3 g/kg of glucose was intraperitoneally administered to the mice after 5 hours or more of fasting at 150 days after implantation, and the increase in human C-Peptide was measured. The plasma C-Peptide level increased significantly in 5 out of 9 glucose challenged mice (FIG. 10B).

The above results demonstrated that the induced pancreatic bud cells administered to mice engrafted in vivo and thereafter functioned to produce insulin in response to the blood glucose level. Accordingly, it was suggested that the induced pancreatic bud cells can be used as a therapeutic agent for insulin hyposecretion.

EXAMPLE 6

Figure 11A:
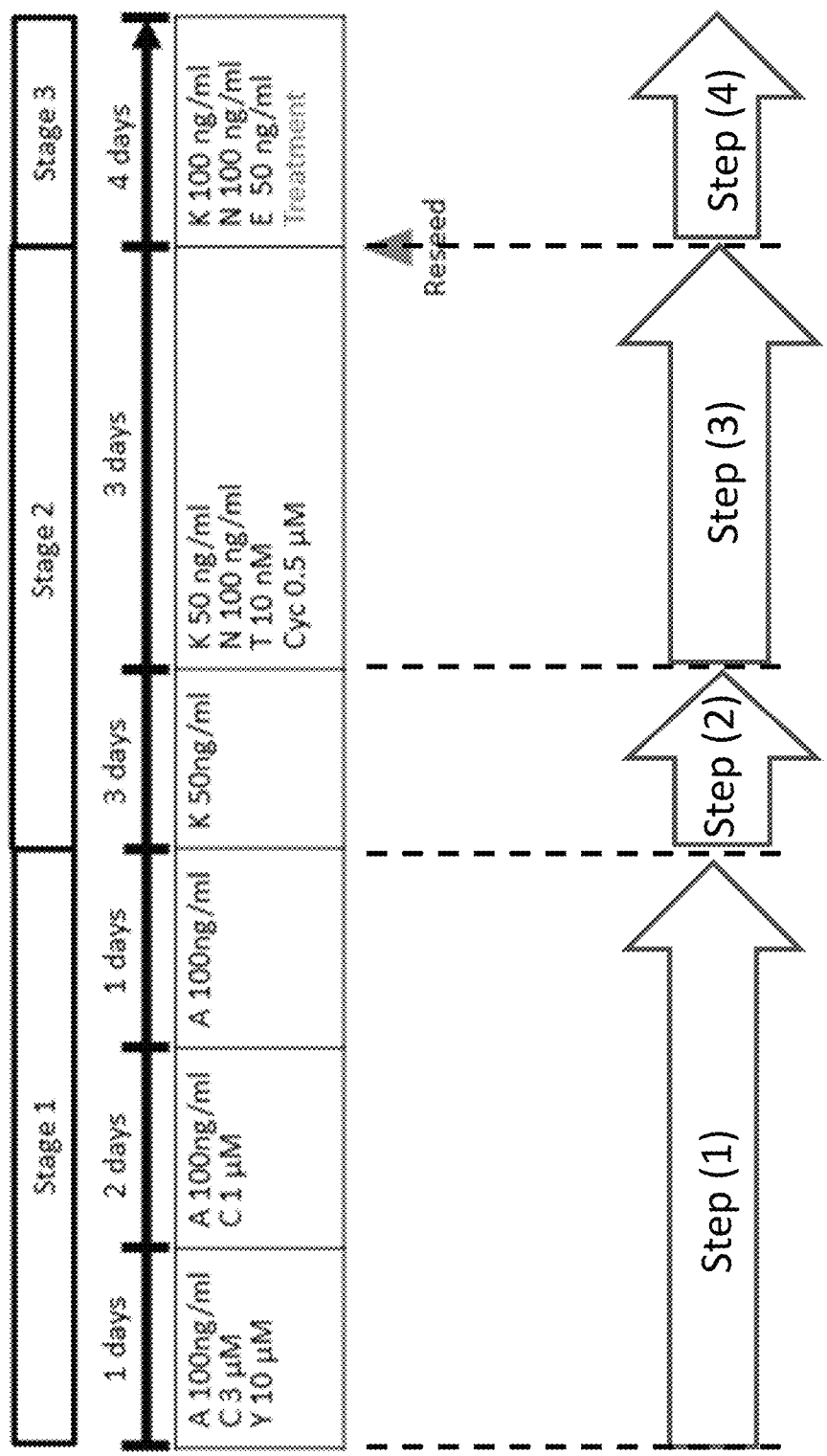
FIG. 11A shows the shows the summary of the protocol for generating pancreatic bud cells from pluripotent stem cells under adhesive conditions.
Figure 11:
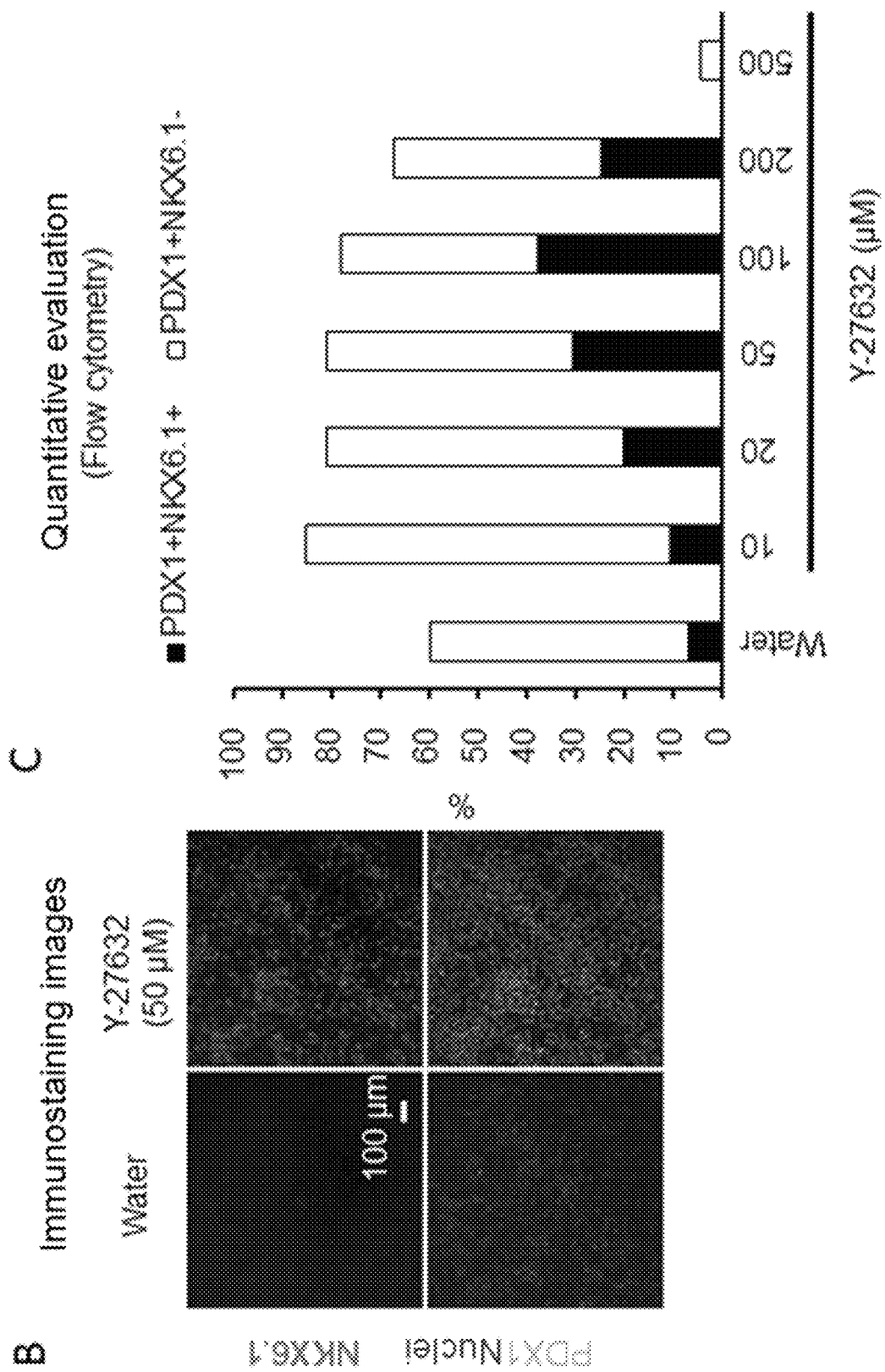
FIG. 11B shows cells obtained by culturing in the presence of 50 μM of Y-27632 during Stage 3 (right) and immunohistochemically stained with pancreatic bud cell markers, PDX1 (lower) and NKX6.1 (upper). In the figure, "Water" (left) indicates the negative control.
FIG. 11C shows the ratio between PDX1$^+$/NKX6.1$^+$ cells and PDX1$^+$/NKX6.1$^-$ cells to the concentration of 1-27632 during Stage 3.

Study on Protocol in Adherent Cultures (FIG. 11A)
(Stage 1)

Cells of iPS cell line 585A1 were seeded on a Matrigel coated 24 well plate at a density of 2.0×10$^5$ cells/well, and cultured in RPMI 1640 Medium (Nacalai Tesque, Inc.) supplemented with 2% B-27 (Life Technologies), 100 ng/ml of activin A (R&D systems), 3 μM of CHIR99021 (Axon Medchem) and 10 μM of Y-27632 (Wako Pure Chemical Industries, Ltd.) for one day. The medium was exchanged with RPMI 1640 Medium containing 100 ng/ml of activin A, 1 μM of CHIR99021 and 2% B-27 (Life Technologies), and the cells were cultured for two days. The medium was then exchanged with RPMI 1640 Medium containing 100 ng/ml of activin A and 2% B-27 (Life Technologies), and the cells were cultured for one day.
(Stage 2)

The medium of the culture obtained in Stage 1 was exchanged with Improved MEM Zinc Option (Invitrogen) containing 50 ng/ml of KGF (R&D systems) and 1% B-27 (Life Technologies) and the cells were cultured for three days. Subsequently, the medium was exchanged with Improved MEM Zinc Option containing 50 ng/ml of KGF, 100 ng/ml of Noggin (Peprotech), 10 nM of TTNPB (Santa Cruz Biotechnology), 0.5 μM of 3-Keto-N-aminoethyl-N'-aminocaproyldihydrocinnamoyl Cyclopamine (KAAD-cyclopamine or K-CYC) (Toronto Research Chemicals) and 1% B-27, and the cells were cultured for three days.
(Stage 3)

The cells obtained in Stage 2 were dissociated into single cells with trypsin, and seeded on a Matrigel coated 24 well plate at a density of 1.6×10$^5$ to 2.4×10$^5$ cells/cm$^2$. Improved MEM Zinc Option containing 100 ng/ml of KGF, 100 ng/ml of Noggin, 50 ng/ml of EGF (R&D systems), various concentration of Y-27632 and 1% B-27 (15×10$^4$ cells/ml) was added to the plate and the cells were cultured for four days.

The obtained cells were treated with BD Cytofix/Cytoperm™ Kit, and thereafter, the ratio of PDX1+NKX6.1+ cells was detected by staining the cells with an anti-PDX1 antibody (R&D systems) and an anti-NKX6.1 antibody (University of Iowa) and analyzing by flow cytometer.

When Y-27632 was used in Stage 3, the ratio of PDX1+ NKX6.1+ cells increased in a concentration-dependent manner, and this effect was highest at 100 μM of Y-27632 (FIGS. 11B and C).

As described above, PDX1+NKX6.1+ cells were produced in adherent culture in the presence of a ROCK inhibitor in Stage 3, after the cells were dissociated.

EXAMPLE 7

Figure 12A:
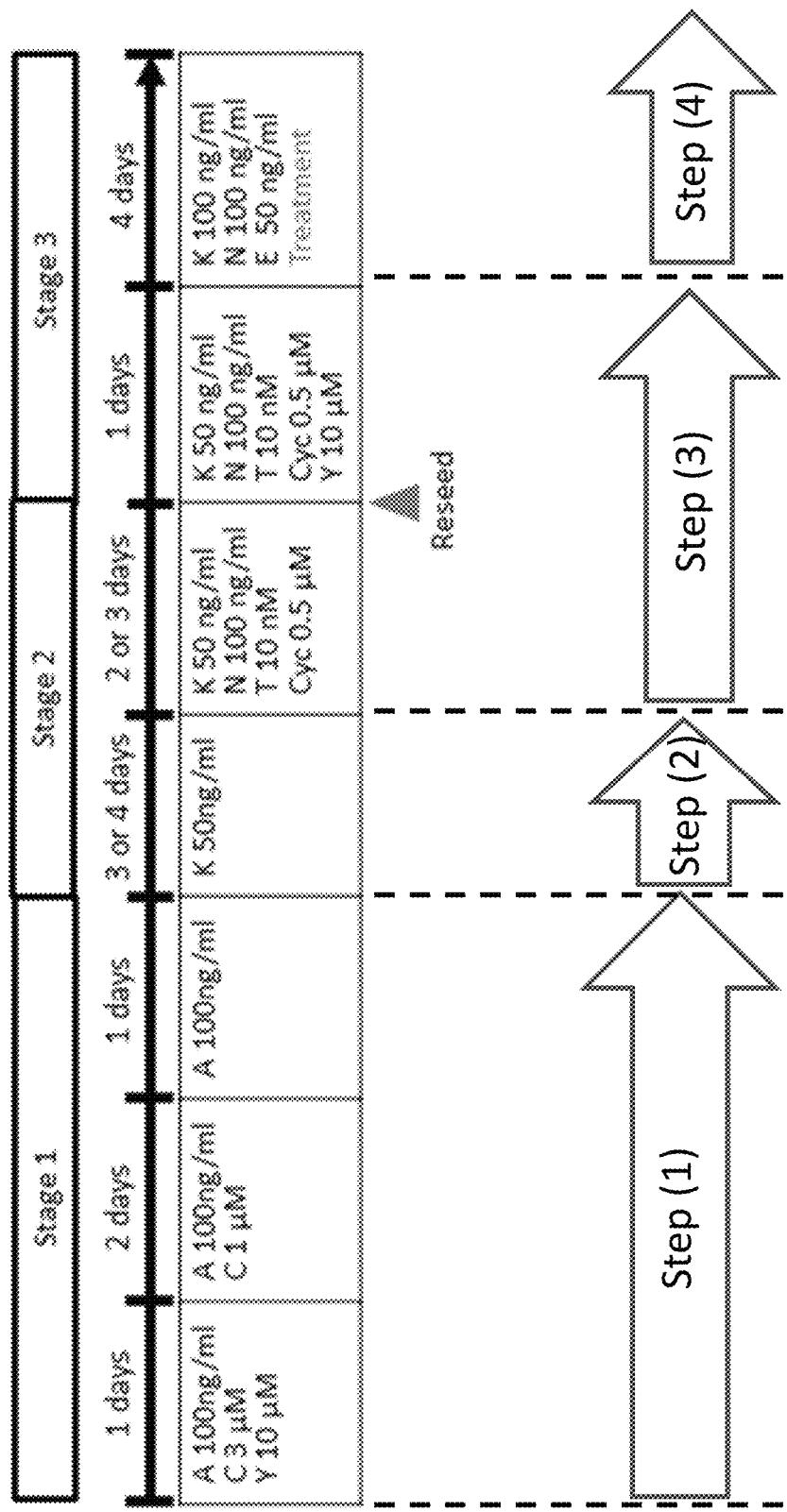
FIG. 12A shows the shows the summary of the modified protocol for generating pancreatic bud cells from pluripotent stem cells under adhesive conditions.
Figure 12:
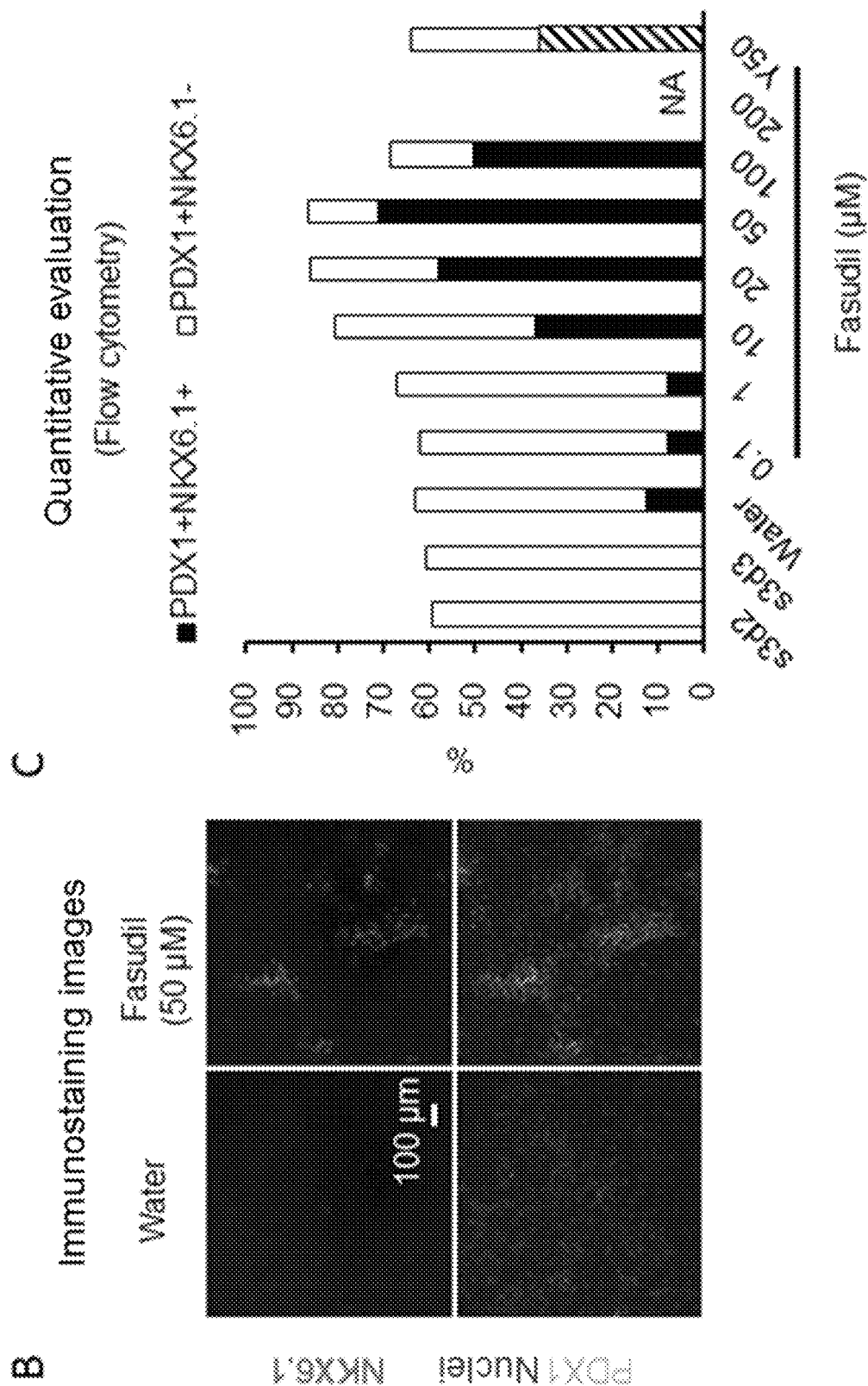
FIG. 12B shows the cells induced by culturing in the presence of 50 μM of Fasudil during Stage 3 in the modified protocol (right), and immunohistochemically stained with pancreatic bud cell markers, PDX1 (lower) and NKX6.1 (upper). In the figure, "Water" (left) indicates negative controls.
FIG. 12C shows the ratio between PDX1-PDX1$^+$/NKX6.1$^+$ cells and PDX1$^+$/NKX6.1$^-$ cells to the concentration of Fasudil during Stage 3. In the figure, "Y50" indicates the ratio of the cells obtained by culturing in the presence of 50 μM of Y-27632 during Stage 3 and is a positive control.

Study on Protocol for Adherent Culture (FIG. 12A) and Additives During Stage 3
(Stage 1)

Cells of iPS cell line 585A1 were seeded on a Matrigel coated 24 well plate at a density of 2.0×10$^5$ cells/well, and the cells were cultured in RPMI 1640 Medium (Nacalai Tesque, Inc.) supplemented with 2% B-27 (Life Technologies), to which 100 ng/ml of activin A (R&D systems), 3 μM of CHIR99021 (Axon Medchem) and 10 μM of Y-27632 (Wako Pure Chemical Industries, Ltd.) were added, for one day. The medium was exchanged with RPMI 1640 Medium containing 100 ng/ml of activin A, 1 μM of CHIR99021 and 2% B-27 (Life Technologies), and the cells were cultured for two days. In addition, the medium was exchanged with RPMI 1640 Medium containing 100 ng/ml of activin A and 2% B-27 (Life Technologies), and the cells were cultured for one day.

(Stage 2)

The medium was exchanged with Improved MEM Zinc Option (Invitrogen) containing 50 ng/ml of KGF (R&D systems) and 1% B-27 (Life Technologies), and the cells were cultured for 3 or 4 days. Subsequently, the medium was exchanged with Improved MEM Zinc Option containing 50 ng/ml of KGF, 100 ng/ml of Noggin (Peprotech), 10 nM of TTNPB (Santa Cruz Biotechnology), 0.5 μM of 3-Keto-N-aminoethyl-N'-aminocaproyldihydrocinnamoyl Cyclopamine (KAAD-cyclopamine or K-CYC) (Toronto Research Chemicals) and 1% B-27 and the cells were cultured for 2 or 3 days.

(Stage 3)

The cells obtained in Stage 2 were dissociated into single cells with trypsin, and the cells were seeded on a Matrigel coated 24 well plate at a density of $1.6 \times 10^5$ to $2.4 \times 10^5$ cells/cm$^2$. Improved MEM Zinc Option containing 50 ng/ml of KGF, 100 ng/ml of Noggin, 10 nM of TTNPB, 0.5 μM of KAAD-cyclopamine, 10 μM of Y-27632 and 1% B-27 was added to the plate, and the cells were cultured for one day. Subsequently, the medium was exchanged with Improved MEM Zinc Option containing 100 ng/ml of KGF, 100 ng/ml of Noggin, 50 ng/ml of EGF (R&D systems), each of compounds (Y-27632, Fasudil (HA-1077), SR3677, GSK269962, H-1152 and Blebbistatin) and 1% B-27 ($15 \times 10^4$ cells/ml) and the cells were cultured for additional 4 days.

The obtained cells were treated with BD Cytofix/Cytoperm™ Kit, stained with an anti-PDX1 antibody (R&D systems) and an anti-NKX6.1 antibody (University of Iowa), and the ratio of PDX1$^+$ cells as well as the ratio of PDX1$^+$NKX6.1$^+$ cells were determined by using a flow cytometer or an image analyzer.

When Fasudil was used in Stage 3, the ratio of PDX1$^+$NKX6.1$^+$ cells increased in a concentration-dependent manner, and this effect was highest at 50 μM of Fasudil (FIGS. 12B and C).

Figure 13:
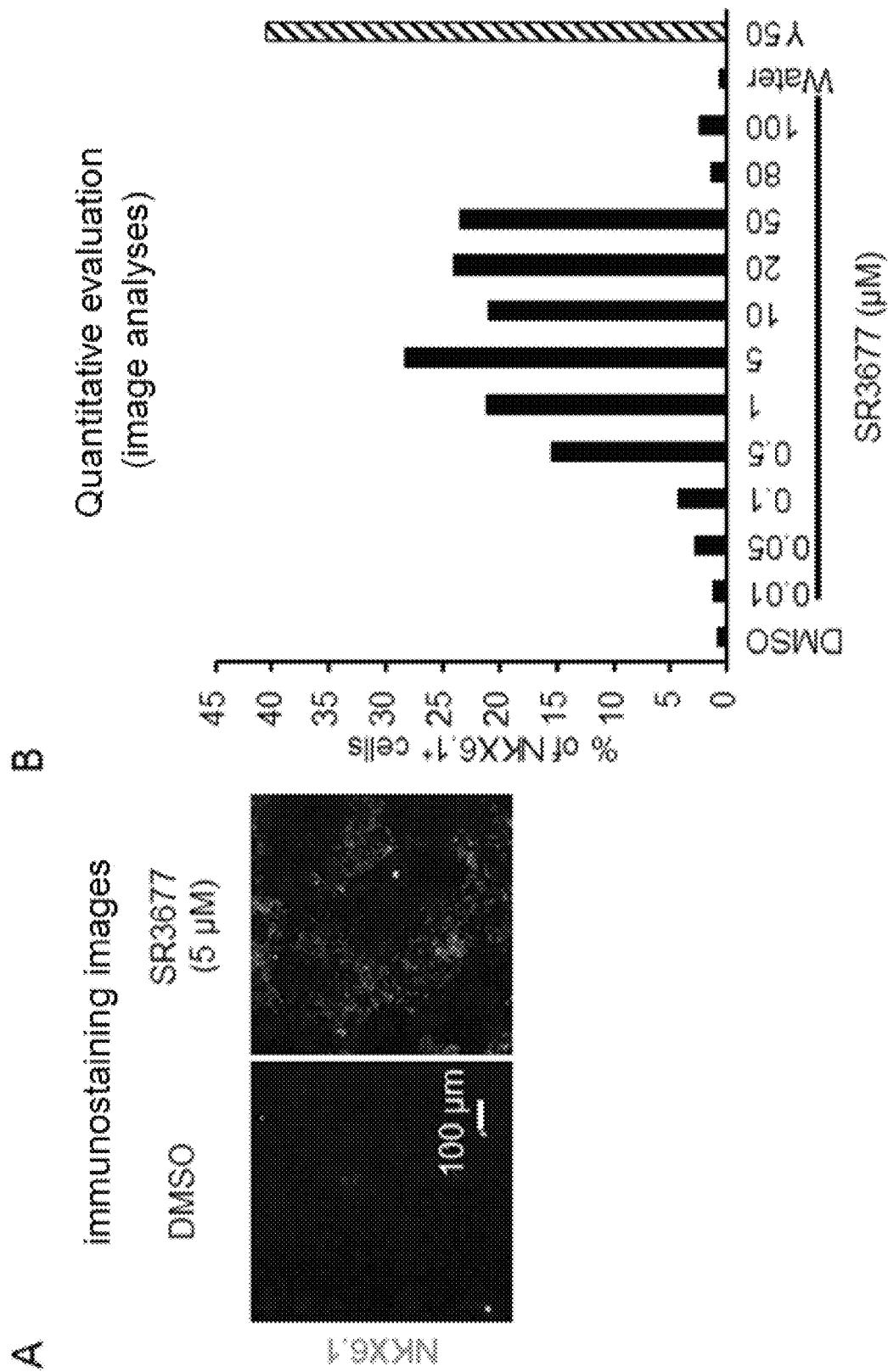
FIG. 13A shows cells obtained by culturing in the presence of 5 μM of SR3677 during Stage 3 in the modified protocol and immunohistochemically stained with NKX6.1. In the figure, "DMSO" (left) indicates a negative control.
FIG. 13B shows the ratio of NKX6.1$^+$ cells in relation to the concentration of SR3677 during Stage 3 in the modified protocol. In the figure, "Y50" indicates the ratio of the cells obtained by culturing in the presence of 50 μM of Y-27632 during Stage 3 and is a positive control.
FIG. 13C shows the cells obtained by culturing in the presence of 0.1 μM of GSK269962 during Stage 3 in the modified protocol and immunohistochemically stained with NKX6.1 (right). In the figure, "DMSO" (left) indicates a negative control.
FIG. 13D shows the ratio of NKX6.1$^+$ cells obtained with each concentration of GSK269962 during Stage 3 in the modified protocol. In the figure, "Y50" indicates the ratio of the cells obtained by culturing in the presence of 50 μM of Y-27632 during Stag 3 in the modified protocol and is a positive control.
Figure 13:
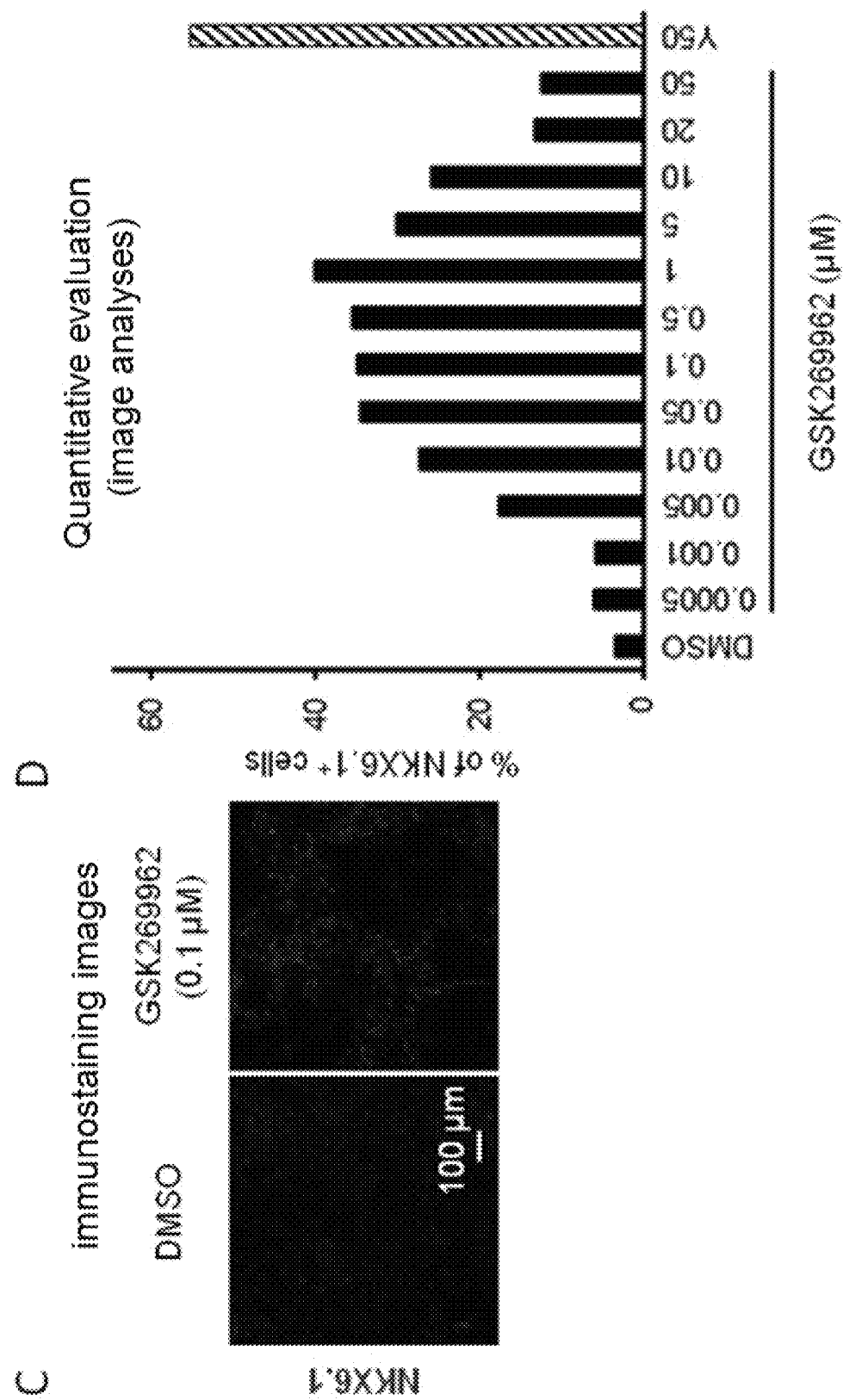

When SR3677 was used in Stage 3, the ratio of NKX6.1$^+$ cells increased in a concentration-dependent manner, and this effect was highest at 5 μM of SR3677 (FIGS. 13A and B).

When GSK269962 was used in Stage 3, the ratio of NKX6.1$^+$ cells increased in a concentration-dependent manner, and this effect was highest at 1 μM of GSK269962 (FIGS. 13C and D).

Figure 14:
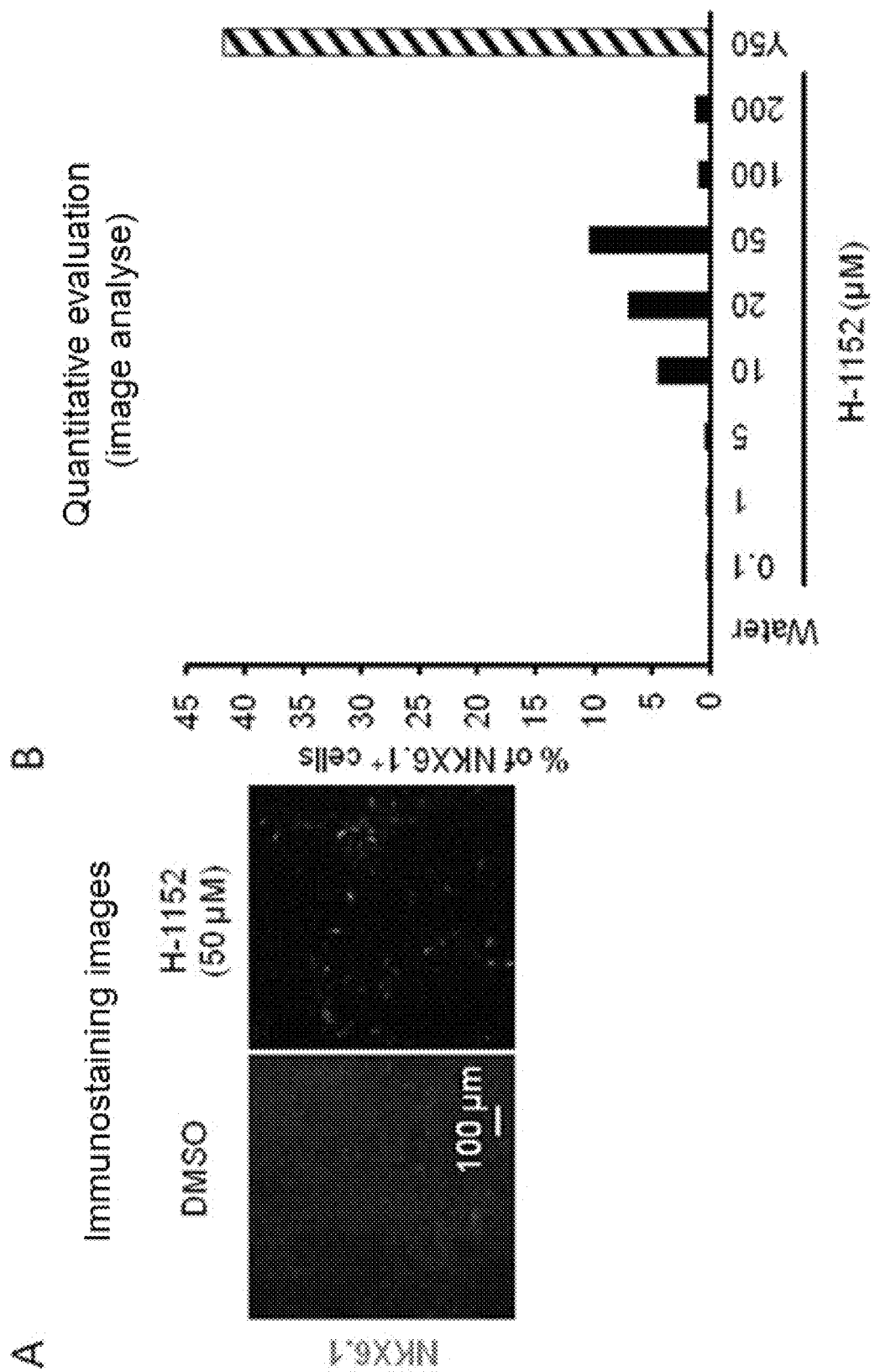
FIG. 14A shows the cells obtained by culturing in the presence of 50 μM of H-1152 (right) during Stage 3 in the modified protocol and immunohistochemically stained with NKX6.1. In the figure, "DMSO" (left) indicates a negative control.
FIG. 14B shows the ratio of NKX6.1$^+$ cells to the concentration of H-1152 during Stage 3 in the modified protocol. In the figure, "Y50" indicates the ratio of the cells obtained by culturing in the presence of 50 μM of Y-27632 during Stag 3 in the modified protocol and is a positive control.
FIG. 14C shows the cells obtained by culturing in the presence of 5 μM of Blebbistatin (right) during Stage 3 in the modified protocol and immunohistochemically stained with pancreatic bud cell markers, PDX1 (lower) and NKX6.1 (upper). In the figure, "DMSO" (left) indicates a negative control.
FIG. 14D shows the ratio of PDX1$^+$/NKX6.1$^+$ cells to concentration of Blebbistatin during Stage 3 in the modified protocol. In the figure, "Y50" indicates the ratio of the cells obtained by culturing in the presence of 50 μM of Y-27632 during Stag 3 in the modified protocol and is a positive control.
Figure 14:
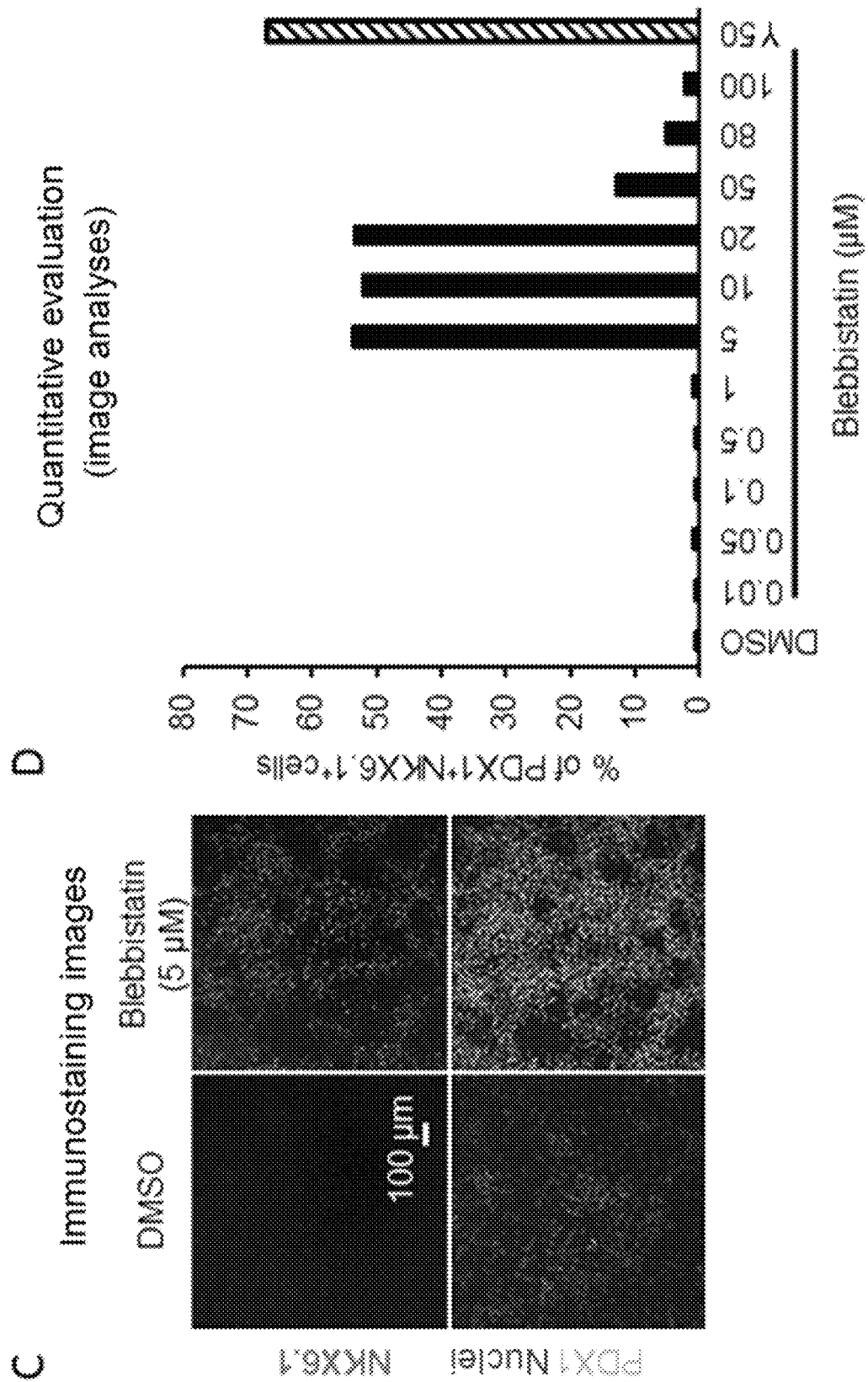

When H-1152 was used in Stage 3, the ratio of NKX6.1$^+$ cells increased in a concentration-dependent manner, and this effect was highest at 50 μM of H-1152 (FIGS. 14A and B).

When Blebbistatin was used in Stage 3, the ratio of PDX1$^+$NKX6.1$^+$ cells increased from 5 μM of Blebbistatin, and this effect was high up to 20 μM of Blebbistatin (FIGS. 14C and D).

As described above, it was confirmed that the cell ratio of PDX1$^+$NKX6.1$^+$ cells increased by decomposing cells, culturing the cells in Stage 3 in adherent cultures by using a similar medium to that used in Stage 2, and adding a ROCK inhibitor or a nonmuscle myosin II inhibitor further in Stage 3.

The invention claimed is:

1. A method for generating pancreatic bud cells from pluripotent stem cells, comprising the following steps:
    (1) culturing the pluripotent stem cells in a medium containing an activin;
    (2) culturing the cells obtained in step (1) in a medium containing KGF;
    (3) culturing the cells obtained in step (2) in a medium containing KGF, a BMP inhibitor, a retinoic acid derivative and a hedgehog pathway inhibitor, wherein the steps (1)-(3) are under an adherent culture condition; and
    (4) dissociating the cells obtained in step (3) into single cells and culturing the dissociated cells under a suspension culture condition in a medium containing KGF, EGF and a BMP inhibitor.

2. The method according to claim 1, wherein the medium containing an activin in step (1) further contains a GSK3 inhibitor.

3. The method according to claim 2, wherein the GSK3 inhibitor is CHIR99021.

4. The method according to claim 1, wherein the BMP inhibitor used in step (3) is Noggin.

5. The method according to claim 1, wherein the retinoic acid derivative is TTNPB.

6. The method according to claim 1, wherein the hedgehog pathway inhibitor is KAAD-cyclopamine.

7. The method according to claim 1, wherein the medium in step (4) further contains a ROCK inhibitor or a nonmuscle myosin II inhibitor.

8. The method according to claim 7, wherein the ROCK inhibitor selected from the group consisting of Y-27632, Fasudil, SR3677, GSK269962, and H-1152; or the nonmuscle myosin II inhibitor is blebbistatin.

9. The method according to claim 8, wherein the ROCK inhibitor is Y-27632 and the concentration of Y-27632 in the medium is 20-100 μM.

10. The method according to claim 1, wherein the medium in step (4) further comprises a TGFβ inhibitor.

11. The method according to claim 1, wherein the TGFβ inhibitor is ALK5 inhibitor II.

12. The method according to claim 1, wherein the pancreatic bud cells are PDX1+ and NKX6.1+.

13. The method according to claim 1, wherein the pluripotent stem cells are human cells.

* * * * *